(12) United States Patent
Drewniak et al.

(10) Patent No.: US 9,371,545 B2
(45) Date of Patent: Jun. 21, 2016

(54) CONSORTIUM AND PREPARATION OF MICROORGANISMS FOR CATALYZING CELLULOSE HYDROLYSIS, PREPARATION FOR METHANE FERMENTATION SUPPLEMENTATION, COMBINATION PREPARATION, USE THEREOF AND METHOD USING THE SAME

(71) Applicant: UNIWERSYTET WARSZAWSKI, Warsaw (PL)

(72) Inventors: Lukasz Drewniak, Warsaw (PL); Krzysztof Poszytek, Minsk Mazowiecki (PL); Martyna Ciezkowska, Minsk Mazowiecki (PL); Aleksandra Sklodowska, Warsaw (PL)

(73) Assignee: UNIWERSYTET WARSZAWSKI, Warsaw (PL)

( * ) Notice: Subject to any disclaimer, the term of this patent is extended or adjusted under 35 U.S.C. 154(b) by 0 days.

(21) Appl. No.: 14/675,171

(22) Filed: Mar. 31, 2015

(65) Prior Publication Data
US 2016/0010114 A1   Jan. 14, 2016

(30) Foreign Application Priority Data

Jul. 11, 2014   (PL) ..................................... 408834

(51) Int. Cl.

| | | |
|---|---|---|
| *C12N 1/20* | (2006.01) | |
| *C12P 1/04* | (2006.01) | |
| *C12P 5/02* | (2006.01) | |
| *C12P 19/02* | (2006.01) | |
| *C12P 19/14* | (2006.01) | |
| *C12P 7/14* | (2006.01) | |

(52) U.S. Cl.
CPC . *C12P 5/023* (2013.01); *C12N 1/20* (2013.01); *C12P 7/14* (2013.01); *C12P 19/02* (2013.01); *C12P 19/14* (2013.01); *C12P 2201/00* (2013.01); *C12P 2203/00* (2013.01)

(58) Field of Classification Search
CPC .............. C12N 1/20; C12R 1/10; C12R 1/01; C12R 1/07; C12P 1/04
See application file for complete search history.

(56) References Cited

FOREIGN PATENT DOCUMENTS

| CN | 103103216 | 5/2013 |
|---|---|---|
| CN | 103146760 | 6/2013 |
| DE | 102009058588 | 8/2011 |
| GB | 2464585 | 4/2010 |
| RU | 2378380 | 1/2010 |
| WO | 2007/014717 | 2/2007 |

OTHER PUBLICATIONS

Polish Search Report dated Aug. 22, 2014, which issued during prosecution of Polish Application No. P. 408834.
Juliana Cardinali-Rezende, et al. "Phylogenetic and physiological characterization of organic waste-degrading bacterial communities" World J. Microbiol Biotechnol 27:245-252, 2011.
Krzysztof Poszytek, et al. "Isolation and characterization of cellulolytic bacteria" 2nd International Conference on Biogas Microbiology ICBM, Jun. 9, 2014.

*Primary Examiner* — Ruth Davis
(74) *Attorney, Agent, or Firm* — Vedder Price P.C.; Thomas J. Kowalski; Deborah L. Lu

(57) ABSTRACT

The invention relates to a consortium of microorganisms capable of hydrolyzing cellulose, preferably lignocellulosic biomass, which may comprise the following mixtures of bacterial strains: *Bacillus* sp. KP7, KP20 and *Ochrobactrum* sp. KP8 (the mixture deposited in PCM under the no. B/00064), *Providencia* sp. KP14; *Bacillus* sp. KP6 and KP16 (the mixture deposited in PCM under the no. B/00065), *Bacillus* sp. KP4, KP5, KP17 and KP22 (the mixture deposited in PCM under the no. B/00066), *Providencia* sp. KP10; *Bacillus* sp. KP1 and KP19 (the mixture deposited in PCM under the no. B/00067), *Ochrobactrum* sp. KP13; *Bacillus* sp. KP9 and KP12 (the mixture deposited in PCM under the no. B/00068), as well as a preparation for hydrolyzing cellulose which may comprise this consortium, a supplement preparation, a combination preparation, and use and method of using the same.

16 Claims, 3 Drawing Sheets

US 9,371,545 B2

CONSORTIUM AND PREPARATION OF MICROORGANISMS FOR CATALYZING CELLULOSE HYDROLYSIS, PREPARATION FOR METHANE FERMENTATION SUPPLEMENTATION, COMBINATION PREPARATION, USE THEREOF AND METHOD USING THE SAME

RELATED APPLICATIONS AND INCORPORATION BY REFERENCE

This application claims benefit of and priority to Polish Patent Application PL408834 filed 11 Jul. 2014.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The invention provides a consortium of microorganisms capable of hydrolyzing cellulose, preferably lignocellulosic biomass, a preparation which may comprise it, use of the consortium of microorganisms and/or the preparation for catalyzing the hydrolysis of cellulose, preferably lignocellulosic biomass and/or increasing the efficiency of biogas production in the methane fermentation process and/or reviving and/or propagating methanogenic consortia, and/or methanogenic microorganisms themselves, which may comprise a use of the consortium of microorganisms capable of hydrolyzing cellulose, preferably lignocellulosic biomass, and/or the preparation which may comprise it. The invention also provides a supplement preparation for reviving and propagating groups of methanogenic microorganisms, produced using the consortium of microorganisms capable of hydrolyzing cellulose, preferably lignocellulosic biomass, and/or the preparation which may comprise it. The invention also provides a combination preparation, which may comprise the consortium of microorganisms capable of hydrolyzing cellulose and/or the preparation which may comprise the consortium, as well as a supplement preparation.

BACKGROUND OF THE INVENTION

Degradation of lignocellulosic biomass is a process used in many branches of industry, mainly in the production of biofuels. Various kinds of energy crops are used to produce high-quality biofuels, such as biogas (biomethane) or bioethanol. The key step, limiting the production of the aforementioned biofuels, is the process of hydrolysis of lignocellulosic material to simpler carbohydrates. In the production of bioethanol, hydrolysis of the plant matter leads to the formation of simple sugars, which undergo alcoholic fermentation. On the other hand, in the production of biogas, plant substrates undergo hydrolysis and then the processes of acidogenesis, acetogenesis and finally methanogenesis. Too slow rate of hydrolysis of lignocellulose leads to stalling of the entire process of degradation of plant biomass and, consequently to the reduction of the efficiency of the fermentation process. On the other hand, excessive hydrolysis of plant substrates can lead to too great an accumulation of intermediate products, which may contribute to system overload and deceleration (or complete inhibition) of the activity of microorganisms carrying out the final stages of biofuel production. The efficiency of hydrolysis and plant biomass degradation processes is dependent on the presence and activity of cellulolytic microorganisms. In agricultural biogas plants and in wastewater treatment plant digesters, the hydrolysis process is dependent on the presence of cellulolytic microorganisms in the input material (i.a. slurry, manure or sewage sludge). If the input material used is poor in cellulolytic microflora, the hydrolysis process will be slow and unstable. Stabilization of an appropriate microflora can take up to several months, which, obviously has a direct impact on the efficiency of the process and on economic benefits.

Currently, the biogas market is trying to respond to the problems caused by the unstable activity of microbial consortia. A great need for a biologically active preparation, which may comprise a stable and well-controlled consortium of microorganisms for the hydrolysis and degradation of lignocellulosic biomass, is observed. Due to the unstable activity and the lack of the ability to control plant biomass degradation, nearly 20% of biogas plants close their operation within the first two years on the market. Preparations that would enable efficient hydrolysis and operation of the process in a controlled manner are sought. Preparations for increasing the viability and efficiency of the microorganisms involved in the production of biogas in the methane fermentation process as well as their revival are also sought.

Microbiological preparations (i.a. produced by German and Danish companies), are available on the biogas market, typically being used for faster ensilage of corn, grass or other batch plants. They are derived from preparations that has been used for preparation of animal feeds for years. Silasil Energy. C, Jbs progas, or AntaSil BG comprise a mixture of bacteria from the genus *Lactobacillus*, whose presence in the silage improves the content of lactic acid, which is a substrate for the microorganisms responsible for methane fermentation. According to the manufacturers' advertising, through such activity, the efficiency of obtaining methane increases by approx. 5%.

In the group of preparations dispensed directly into digesters, mainly mineral supplements of methane fermentation are found. Products such as IPUSmeth-Max are mixtures of micronutrients and substances buffering the resulting ammonia, too high concentrations of which is a methanogenesis inhibitor. According to the manufacturer, its use can bring up to 10% increase of the efficiency of methane production, but it requires constant expenses to purchase the preparation, the dosage of which should be almost daily. In this group, one of the very few products containing microorganisms is Anta-Ferm BG, consisting of both cultures of microorganisms and trace elements. In the case of using the above preparations, investments of 25-42 euros per 30 tons of input are required. These are expensive solutions, which do not always give a radical improvement in the functioning of the biogas plant.

Preparations intended directly for plant biomass hydrolysis are also known. These are enzymatic preparations which are stable, but they are usually specific for a particular pool of substrates, because they are derived from one strain (typically from fungi). Moreover, such preparations are expensive, because they must be systematically and regularly added to the working biogas plant. Such preparations include, among others, Celuferm (Eurozyme) and BG Max (Novozymes).

Currently preparations for the hydrolysis of lignocellulosic biomass, which: (i) after a single addition, would ensure long-term and stable operation of the biogas plant, (ii) would be relatively inexpensive, (iii) would have a broad spectrum of activity, would be universal and resistant to the changing environmental conditions, are sought. In summary, preparations employing a bacterial biomass, capable of propagation using the utilized lignocellulosic material are sought. Thus, preparations, which will increase the viability of methanogenic microorganisms and eventually support the efficiency of gas production by methanogenic microorganisms using lignocellulosic material are also sought.

Citation or identification of any document in this application is not an admission that such document is available as prior art to the present invention.

SUMMARY OF THE INVENTION

The invention provides a consortium of microorganisms capable of hydrolyzing cellulose, preferably lignocellulosic biomass, which may comprise the following mixtures of bacterial strains, which have been deposited on the 14 May 2014 in the Polish Collection of Microorganisms (PCM) of the Institute of Immunology and Experimental Therapy, Polish Academy of Sciences, in Wroclaw, Poland: *Bacillus* sp. KP7, KP20 and *Ochrobactrum* sp. KP8 (Digest-Prep A—a mixture deposited under the no. B/00064), *Providencia* sp. KP14; *Bacillus* sp. KP6 and KP16 (Digest-Prep B—a mixture deposited under the no. B/00065), *Bacillus* sp. KP4, KP5, KP17 and KP22 (Digest-Prep C—a mixture deposited under the no. B/00066), *Providencia* sp. KP10; *Bacillus* sp. KP1 and KP19 (Digest-Prep D—a mixture deposited under the no. B/00067). *Ochrobactrum* sp. KP13; *Bacillus* sp. KP9 and KP12 (Digest-Prep E—a mixture deposited under the no. B/00068). The consortium according to the invention was named the Digest-Prep consortium.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSITS

Mixtures of bacterial strains have been deposited on the 14 May 2014 in the Polish Collection of Microorganisms (PCM) of the Institute of Immunology and Experimental Therapy, Polish Academy of Sciences, in Wroclaw, Poland: *Bacillus* sp. KP7, KP20 and *Ochrobactrum* sp. KP8 (Digest-Prep A—a mixture deposited under the no. B/00064), *Providencia* sp. KP14; *Bacillus* sp. KP6 and KP16 (Digest-Prep B—a mixture deposited under the no. B/00065), *Bacillus* sp. KP4, KP5, KP17 and KP22 (Digest-Prep C—a mixture deposited under the no. B/00066), *Providencia* sp. KP10; *Bacillus* sp. KP1 and KP19 (Digest-Prep D—a mixture deposited under the no. B/00067), *Ochrobactrum* sp. KP13; *Bacillus* sp. KP9 and KP112 (Digest-Prep E—a mixture deposited under the no. B/00068). The consortium according to the invention was named the Digest-Prep consortium.

The Deposits with Polish Collection of Microorganisms (PCM) of the Institute of Immunology and Experimental Therapy, Polish Academy of Sciences, in Wroclaw, Poland, under deposit accession numbers B/00064, B/00065, B/00066, B/00067 and B/00068 were made pursuant to the terms of the Budapest Treaty. Upon issuance of a patent, all restrictions upon the deposit will be removed, and the deposit is intended to meet the requirements of 37 CFR §§1.801-1.809. The deposit will be irrevocably and without restriction or condition released to the public upon the issuance of a patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

For a better understanding of the invention, it has been illustrated by the embodiments and in the accompanying figures.

DETAILED DESCRIPTION OF THE INVENTION

Figure 1:
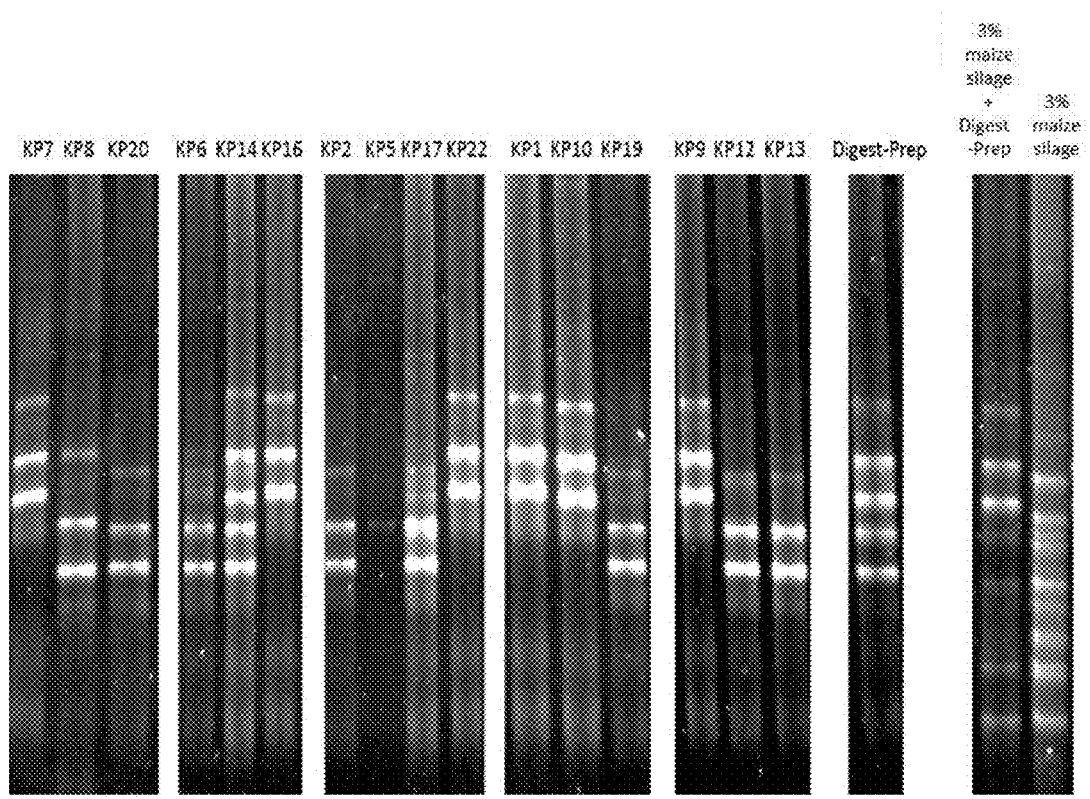
FIG. 1 shows the results of DGGE electrophoretic separation for: pure cultures being the components of the mixtures Digest-Prep A, Digest-Prep B, Digest-Prep C, Digest-Prep D, Digest-Prep E; the Digest-Prep consortium; the Digest-Prep consortium grown at 3% corn silage, and indigenous microflora present in corn silage, which is used as a substrate in the experiments.

In the preferred embodiments of the present invention, particular strains in each mixture are mixed in equal proportions. Preferably all the prepared mixtures are combined at an equal quantitative ratio.

The invention also provides a preparation named Digest-Prep for catalyzing the hydrolysis of cellulose, preferably lignocellulosic biomass and/or increasing the efficiency of biogas production in the methane fermentation process and/or reviving and/or propagating methanogenic consortia, and/or methanogenic microorganisms themselves, which may comprise the consortium of microorganisms according to the invention. Preferably, such preparation also may comprise supplementary and/or auxiliary substances.

The present invention is based on a mixture of strains developed by the inventors and the preparation which may comprise it, named Digest-Prep which may comprise Digest-Prep A—the mixture deposited under the no. B/00064, Digest-Prep B—the mixture deposited under the no. B/00065, Digest-Prep C—the mixture deposited under the no. B/00066, Digest-Prep D—the mixture deposited under the no. B/00067, Digest-Prep E—the mixture deposited under the no. B/00068) for the hydrolysis of cellulose, preferably lignocellulosic biomass. The Digest-Prep preparation may comprise a consortium including 16 strains of bacteria specialized in lignocellulosic biomass degradation, isolated from different environments (agricultural biogas plant hydrolyzer from Miedzyrzec Podlaski, raw sludge from the wastewater treatment plant Czajka in Warsaw, slurry and cattle manure from farm households in Niemoglowy and Trzebieszow Pierwszy). The consortium consists of strains selected from strains representing the bacteria of the genera *Bacillus, Ochrobactrum*, and *Providencia*. The invention is based upon an unexpected finding that the bacterial strains isolated from the aforementioned environments, which are part of the consortium according to the invention and the Digest-Prep preparation according to the invention are characterized by a high activity of cellulose degradation (determined on the basis of tests with carboxymethylcellulose) and the ability to function in a broad range of stress factors (under aerobic and anaerobic conditions, at pH 4-10, temperature, salinity). The Digest-Prep consortium and the Digest-Prep preparation accelerate the degradation of lignocellulosic biomass, releasing many organic compounds and allowing supplementation of the fermentation and increase of the biogas production by 10 to 40%, depending on the substrate used.

The present invention also relates to a supplement preparation named Supp-Digest-Prep for supplementation of methane fermentation, which may comprise organic and inorganic substances derived from the degradation of biomass produced using a consortium of microorganisms, and which is produced using the consortium of microorganisms according to the invention and/or the preparation which may comprise the consortium according to the invention. Such preparation supports the viability and efficiency of methanogenic microorganisms. The consortium of microorganisms and/or the preparation according to the invention can provide effective hydrolysis of cellulose, preferably lignocellulosic biomass and/or increase in the efficiency of biogas production, even after a single administration, also having influence on the supporting of viability and efficiency of methanogenic microorganisms.

In another aspect, the invention may comprise the use of the consortium of microorganisms according to the invention and/or the preparation according to the invention for catalyzing the hydrolysis of cellulose, preferably lignocellulosic biomass. Preferably, the consortium of microorganisms and/or the preparation are used directly in digesters. In the preferred embodiment, the use according to the invention leads to increase in the efficiency of biogas production in the methane fermentation process. In another aspect of the invention, the Digest-Prep consortium and preparation according to the invention enable the production of methane fermentation supplements, which increase the efficiency of biogas production by up to 40%, and decrease the retention time in the digester.

In one of the embodiments the Digest-Prep consortium and/or preparation according to the invention are used for manufacturing a supplement preparation for supplementation of methane fermentation, named the Supp-Digest-Prep preparation. In the preferred embodiment, the supplement preparation for supplementing methane fermentation according to the invention may comprise the supernatant obtained after centrifugation of cultures of bacterial strains included in the consortium of microorganisms according to the invention and/or the preparation which may comprise the consortium according to the invention.

Preferably, the supplement preparation for supplementation of the methane fermentation according to the invention is added to the medium for methanogenic consortia, and/or methanogenic microorganisms themselves at a ratio of 1:2.0 of the medium. In another aspect of the invention, the Digest-Prep consortium according to the invention and/or the Digest-Prep preparation which may comprise the consortium according to the invention and/or the Supp-Digest-Prep supplement preparation for supplementation of the methane fermentation according to the invention, are used for reviving and/or propagating methanogenic consortia and/or methanogenic microorganisms themselves, including methanogenic archaea. Thus, the invention also relates to the use of the consortium of microorganisms according to the invention and/or the preparation according to the invention and/or the supplement preparation according to the invention and/or the Supp-Digest-Prep-Plus combination preparation according to the invention for reviving and/or propagating methanogenic consortia, and/or methanogenic microorganisms themselves.

The invention also relates to the Supp-Digest-Prep-Plus combination preparation for catalyzing the hydrolysis of cellulose, preferably lignocellulosic biomass and/or increasing the efficiency of biogas production in the methane fermentation process and/or reviving and/or propagating methanogenic consortia, and/or methanogenic microorganisms themselves. The Supp-Digest-Prep-Plus combination preparation which may comprise the consortium and/or the Digest-Prep preparation in combination with the supplement preparation, Supp-Digest-Prep, and is used for supporting the viability of methanogenic microorganisms and productivity of methanogenic microorganisms, supplementing methane fermentation and ensuring effective hydrolysis of cellulose, preferably lignocellulosic biomass and/or increasing the efficiency of biogas production, (preferably after a single administration.

The Supp-Digest-Prep-Plus combination preparation used for enhancing viability and supplementing methane fermentation yields a synergistic effect and mediates an increase in the production of biogas by 25 to 48% and methane concentration in the obtained biogas by even 75%, and a decrease of the retention time in the digester (what directly affects the speed of the conducted process).

The invention also relates to a method of catalyzing the hydrolysis of cellulose, preferably lignocellulosic biomass, which may comprise the use of the Digest-Prep consortium of microorganisms according to the invention and/or the Digest-Prep preparation according to the invention and/or the Supp-Digest-Prep-Plus combination preparation according to the invention. In the preferred embodiment of the method, the use of the consortium and/or the preparation according to the invention and/or the combination preparation according to the invention leads to the supporting of viability and productivity of methanogenic microorganisms and increase in the efficiency of biogas production in the methane fermentation process.

Preferably, in the method according to the invention, the consortium of microorganisms and/or the preparation according to the invention, are used directly in the digesters.

In a preferred embodiment, the hydrolysis is carried out under anaerobic conditions at 30° C.

In a preferred embodiment, the hydrolysis is carried out at pH=7.

In a preferred embodiment, the consortium of microorganisms and/or the preparation according to the invention are used together with the methanogenic consortium.

The invention also relates to a method of reviving and/or propagating methanogenic consortia, and/or methanogenic microorganisms themselves, which may comprise the use of the consortium of microorganisms according to the invention (the Digest-Prep consortium) and/or the preparation according to the invention (the Digest-Prep preparation) and/or the preparation for supplementation of the methane fermentation according to the invention (the Supp-Digest-Prep preparation) and/or the combination preparation according to the invention (the Supp-Digest-Prep-Plus preparation).

To prepare the Digest-Prep consortium and/or preparation according to the invention, five smaller mixtures of the Digest-Prep strains A, B, C, D and/or E must first be prepared, each of which is composed of several different microbial cultures. The mixtures may comprise the following cultures:

Digest-Prep A: *Bacillus* sp, KP7, KP20; *Ochrobactrum* sp. KP8 (the mixture deposited in PCM under the no. B/00064)

Digest-Prep B: *Providencia* sp. KP14; *Bacillus* sp. KP6, KP16 (the mixture deposited in PCM under the no. B/00065)

Digest-Prep C: *Bacillus* sp. KP4, KP5, KP17, KP22 (the mixture deposited in PCM under the no. B/00066)

Digest-Prep D: *Providencia* sp. KP10; *Bacillus* sp. KP1, KP19 (the mixture deposited in PCM under the no. B/00067)

Digest-Prep E: *Ochrobactrum* sp. KP13; *Bacillus* sp. KP9, KP12 (the mixture deposited in PCM under the no. B/00068)

In all the cases, the procedure tier preparing components of the mixtures is identical. This procedure is based on the obtaining of pure cultures of bacteria in a liquid medium with cellulose or derivative thereof, as the sole source of carbon. On the basis of the growth period of bacteria in the medium, the number of cells can be determined by known techniques (for example by fluorescence staining with DAPI dye) and the particular strains can be mixed, preferably in equal proportions. The density of cells in each of the Digest-Prep mixtures (A, B, C, D, E) is preferably about $10^7$-$10^8$. The so prepared mixture/s of microorganisms can be stored using the methods known in the art, for example, after lyophilization.

In order to Obtain the Digest-Prep cellulolytic consortium, all the prepared mixtures should be mixed together, preferably in an equal quantitative ratio (so as the number of cells per ml of each strain in each mixture was the same). The Digest-Prep preparation can be further supplemented with additional supplementary, auxiliary, stabilizing substances, etc. The added substances may also affect e.g. the obtaining of a high density of biomass, maintaining an increased biochemical activity, increase in the access to nutrients or additionally increase in the survival rate.

In order to obtain the preparation for the supplementation of methane fermentation, named the Supp-Digest-Prep preparation, culture of microorganisms included in the Digest-Prep consortium and/or the preparation according to the invention must be carried out, and subsequently, the supernatant from this culture should be obtained by methods known in the art, for example, by centrifugation. The obtained supernatant should be sterilized. The so-obtained preparation for the supplementation of methane fermentation can be used to supplement the medium for methanogenic consortia, as well as methanogenic microorganisms themselves, including methanogenic archaea.

The term "consortium" or "consortium of microorganisms", as used herein is intended to mean a group of bacterial strains capable of growing together, and interacting in lignocellulose degradation.

The term "consortium", also called the Digest-Prep consortium, as used herein is intended to mean a group of 16 strains (forming the Digest-Prep mixtures: A—the mixture deposited in PCM under the no. B/00064, B—the mixture deposited in PCM under the no, B/00065, C—the mixture deposited in PCM under the no. B/00066, D—the mixture deposited in PCM under the no. B/00067, E—the mixture deposited in PCM under the no. B/00068), capable of growing together, and interacting in lignocellulose degradation.

The term "preparation", also called the Digest-Prep preparation, as used herein is intended to mean a mixture which may comprise the Digest-Prep consortium and supplementary and/or auxiliary substances. The supplementary and/or auxiliary substances can be for example any media components, carriers, stabilizers, supplements for culturing bacteria, and mixtures thereof known in the art.

The term "supplement preparation", also called the Supp-Digest-Prep preparation or Supp-Digest-Prep, as used herein is intended to mean a sterile solution containing organic (i.a. volatile fatty acids, sugars, vitamins) and inorganic substances (i.a. ammonia, phosphates) deriving from the degradation of biomass, preferably plant biomass, most preferably from the degradation of corn silage, using the Digest-Prep consortium or preparation according to the invention.

The term "combined preparation", also called Supp-Digest-Prep or the Supp-Digest-Prep preparation, as used herein is intended to mean a mixture of the Digest-Prep consortium of microorganisms and/or the Digest-Prep preparation according to the invention with the Supp-Digest-Prep preparation. Such a combined preparation, named Supp-Digest-Prep-Plus will be used for catalyzing the hydrolysis of cellulose, preferably lignocellulosic biomass and/or increasing the efficiency of biogas production in the methane fermentation process and/or reviving and/or propagating methanogenic consortia, and/or the methanogenic microorganisms themselves.

Publications cited in the description, and the references given therein, are in their entirety incorporated herein as references.

The following examples are presented merely to illustrate the invention and to clarify its various aspects, but are not intended to be limitative, and should not be equated with all its scope, which is defined in the appended claims.

In the following examples, unless it was otherwise indicated, standard materials and methods described in Sambrook and Russell. 2001. Molecular cloning: A laboratory manual. Cold Spring Harbor Laboratory Press, New York. were used, or the manufacturers' instructions for specific materials and methods were followed.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Selection and Identification of Bacterial Strains with an Increased Hydrolytic Activity of Lignocellulosic Biomass Bacteria capable of degrading cellulose were isolated from inoculum samples from: (i) agricultural biogas plant hydrolyser from Miedzyrzec Podlaski, (ii) raw sludge from the wastewater treatment plant Czajka in Warsaw, (iii) slurry and cattle manure from farm households in Niemglowy and Trzebieszow Pierwszy. Selection was performed using the modified minimal medium of the following composition: peptone 5 g/l; yeast extract 5 g/l; NaCl 5 g/l; $KH_2PO_4$ 1 g/l; $MgSO_4$ 0.2 g/l; carboxymethylcellulose (CMC) 10 g/l; pH 7.0 (Bushnell and Haas, 1941). Cultures were carried out in 200 ml of the medium with the addition of 0.5% of dry weight of the initial inoculum, at 30° C., 120 rpm for 72 hours. Subsequently, the culture was passaged onto minimal medium with CMC. After each of the 6 passages made, bacteria were plated on minimal medium with CMC solidified with agar, and incubated for 72 hours at 30° C. Pure cultures, characterized by varying morphology were selected by replica method onto a fresh medium. From all the conducted cultures, a pool of ~100 pure cultures was obtained. Strains which were characterized by an increased ability to degrade carboxymethylcellulose were selected for further analysis. Preliminary studies on the CMC degradation activity were carried out on a modified medium with carboxymethylcellulose and Congo Red of the following composition: $KH_2PO_4$ 0.5 g/l; $MgSO_4$ 0.25 g/l; carboxymethylcellulose 2 g/l; gelatin 2 g/l; Red Congo 0.2 g/l. The pH of the medium was adjusted to 6.8-7.2 and solidified with agar 15 g/l (Hendricks et al., 1995). The use of Congo Red as indicator and an inductor of cellulose degradation on solid medium constitutes the basis for a rapid and sensitive assay for cellulolytic bacteria. Discolorations around a colony indicate a positive result regarding the degradation. After the initial selection a pool of ~50 strains capable of degrading CMC and characterized by an increased cellulolytic activity (i.e. clear zones on CMC+Congo Red medium were >15 mm) was obtained (Tab. 2). The next step was the elimination of the same strains. For this purpose, Amplified Ribosomal DNA Restriction Analysis (ARDRA) was used. Each of the investigated strains was subjected to the so-called rapid cell lysis in lysis buffer (0.05M NaOH, 0.25% SDS). Subsequently, the resulting lysate was used as template DNA in the amplification of the 16S rRNA gene using the primers 27F and 1492R (Lane, 1991). The obtained PCR products were digested with HaeIII enzyme and electrophoretic analysis was performed. Based on this, unique strains, representing each of the selected environments (hydrolyzer, slurry, manure) were chosen (Tab. 1)

In order to identify the selected strains, 16S rRNA genes of each strain were amplified, cloned in the pGEM-T-Easy vector, and then sequenced. Sequencing was performed using the primers 27F and 1492R. Computer analyses included the processing of the obtained sequences using programs: FinchTV ver. 1.4; Clone Manager Professional Suite ver. 8.0; Blast (http://blast.ncbi.nlm.nih.gov/). The sequences of the 16S rRNA genes of the identified strains were deposited in the GenBank database, NM. The results of the identification of pure cultures are presented in Table 1.

TABLE 1

Identification of bacteria included the "DigestPrep" consortium, degrading lignocellulosic biomass

| Strain no. (accession number in GenBank) | Origin (site of isolation) | Classification based on the analysis of 16S rDNA | | |
|---|---|---|---|---|
| | | Organism (accession number in GenBank) | Identity (%) | 16S rDNA sequence (SEQ ID. NO) |
| KP1 (KJ777134) | Biogas plant hydrolyzer Miedzyrzec Podlaski | *Bacillus licheniformis* strain Pb-HK09002 (HM006898.1) | 99 | 1 |
| KP16 (KJ777149) | Biogas plant hydrolyzer Miedzyrzec Podlaski | *Bacillus aerius* strain RGS230 (KC469617.1) | 99 | 12 |
| KP22 (KJ777154) | Biogas plant hydrolyzer Miedzyrzec Podlaski | *Bacillus licheniformis* strain AnBa7 (AY887129.1) | 99 | 16 |
| KP4 (KJ777137) | Cattle manure Niemglowy | *Bacillus pumilus* strain SAFR-032 (NR_074977.1) | 98 | 2 |

TABLE 1-continued

Identification of bacteria included the "DigestPrep" consortium, degrading lignocellulosic biomass

| Strain no. (accession number in GenBank) | Origin (site of isolation) | Classification based on the analysis of 16S rDNA | | |
|---|---|---|---|---|
| | | Organism (accession number in GenBank) | Identity (%) | 16S rDNA sequence (SEQ ID. NO) |
| KP5 (KJ777138) | Cattle manure Niemglowy | Bacillus pumilus strain Jo2 (KF734912.1) | 99 | 3 |
| KP6 (KJ777139) | Cattle manure Niemglowy | Bacillus pumilus strain 43 (KF923453.1) | 99 | 4 |
| KP7 (KJ777140) | Cattle manure Niemglowy | Bacillus altitudinis strain EH36 (GU3339265.1) | 96 | 5 |
| KP8 (KJ777141) | Cattle manure Niemglowy | Uncultured Ochrobactrum sp. clone DM11-150 (KC172366.1) | 98 | 6 |
| KP9 (KJ777142) | Cattle manure Niemglowy | Bacillus sp. B2066 (JX266376.1) | 99 | 7 |
| KP10 (KJ777143) | Cattle manure Niemglowy | Providencia vermicola strain FFA6 (JN092794.1) | 99 | 8 |
| KP12 (KJ777145) | Cattle manure Niemglowy | Uncultured Bacillus sp. clone Filt.123 (HM152710.1) | 99 | 9 |
| KP17 (KJ777150) | Cattle manure Niemglowy | Bacillus subtilis isolate SCS-3 (EU257431.1) | 99 | 13 |
| KP13 (KJ777146) | Cattle manure Trzebieszow Pierwszy | Uncultured Ochrobactrum sp. clone DM11-150 (KC172366.1) | 98 | 10 |
| KP14 (KJ777147) | Cattle manure Trzebieszow Pierwszy | Providencia vermicola strain FFA6 (JN092794.1) | 95 | 11 |
| KP19 (KJ777151) | Cattle manure Trzebieszow Pierwszy | Bacillus pumilus strain 38 (KF923448.1) | 99 | 14 |
| KP20 (KJ777152) | Cattle manure Trzebieszow Pierwszy | Uncultured Bacillus sp. clone Filt.123 (HM152710.1) | 99 | 15 |

Example 2

Determination of the Activity of Extracellular Cellulolytic Enzymes

In order to show that the selected strains are characterized by a high cellulolytic activity, a detailed, quantitative assay of the activity of cellulolytic enzymes was carried out using the modified method developed by Ghose T. K. (1987). Cellulolytic activity was determined indirectly based on the quantity of reducing sugars (glucose) in the reaction mixture, resulting from the hydrolysis of carboxymethylcellulose by enzymes secreted from the selected microorganisms cultured on minimal medium with CMC. To 0.5 ml of double-diluted culture supernatant an equal volume of 2% solution of carboxymethylcellulose was added, and incubated for 30 minutes at 50° C. After the incubation, 3 ml of 3,5-dinitrosalicylic acid (DNS) were added to the reaction mixture and it was incubated again for 5 minutes in boiling water. Subsequently, the samples were cooled and 20 ml of distilled water were added, and vigorously mixed. Absorbance of the reaction mixture was measured at a wavelength of 540 nm. Glucose standards in the range of 0.5-2 mg/ml and a blank, to which, instead of the culture, 0.1 M of sodium acetate of pH 5.5 was added, were prepared analogously to the method above. The amount of reducing sugars was determined from the standard curve constructed as the dependency of absorbance on the amount of glucose. The enzymatic activity of endoglucanase (CMCase) is defined in international units (IU). One unit of enzymatic activity is defined as the amount of enzyme which releases 1 µmol of reducing sugars (measured as glucose) per ml within 1 minute. Cellulolytic activity was determined for the pure cultures as well as for the mixture of strains, included in the consortium labelled as Digest-Prep.

Among the 16 isolated bacterial strains there are microorganisms characterized by increased endoglucanase cellulolytic activity (Tab. 2). The range of activity for all the strains was from 0.127 IU/ml the KP11 strain, to 0.547 IU/ml for the KP16 strain. The KP16, KP22 strains, isolated from the agricultural biogas plant hydrolyzer and the KP19 strain, from cattle manure, are characterized by the highest activity of extracellular enzymes. All these bacteria belong to the Bacillus genus.

For comparison, exemplary literature data report that the CMCase activity for the reference cellulolytic strain Cellulomonas sp. ASN2 may be about 0.400 IU/ml, depending on the composition and pH of the medium, as well as the temperature at which the cultures were carried out.

The results of cellulolytic activity, obtained by carrying out the cultures of strains on the medium with carboxymethylcellulose as the sole source of carbon, pH 7, at 30° C., are shown in Tab. 2. In the case of the results of cellulolytic activity obtained on the basis of the test carried out on the medium with Congo Red as the inducer for degradation of cellulose, the results obtained differed from those for CMCase. The basis of the test was the investigation of the size of clear zones around the colonies of bacteria. All the results were higher than the minimal value found in the literature, i.e. 15 mm. The highest results were obtained for the strains KP1, KP20, KP22, KP16. Lack of correlation between the results of the two variants of the cellulolytic activity studies, may be explained by the technique of the performed tests and the main principle of action. In the case of CMCase, the amount of the end product formed as a result of action of cellulolytic enzymes was investigated, whereas in the case of the test with Congo Red in the medium, the result may depend on the diffusion of the enzymes in the medium, the amount of the enzymes, or the size of the colony.

TABLE 2

The results of cellulolytic activity and the optimal conditions for the growth of the selected bacteria.

| | Cellulolytic activity | | Optimal conditions for growth | | |
|---|---|---|---|---|---|
| Strain no. | CMCase [IU/ml] | Clear zones on the Red-Congo medium [mm] | pH (4-10) | Temperature (23-45° C.) | CMC concentration (0.5-2%) |
| KP1  | 0.319 | 44 | 7  | 30 | 2%   |
| KP16 | 0.547 | 33 | 7  | 37 | 2%   |
| KP22 | 0.495 | 35 | 7  | 30 | 1%   |
| KP4  | 0.396 | 27 | 10 | 30 | 2%   |
| KP5  | 0.344 | 15 | 7  | 37 | 2%   |
| KP6  | 0.494 | 26 | 10 | 30 | 2%   |
| KP7  | 0.442 | 22 | 10 | 37 | 2%   |
| KP8  | 0.216 | 17 | 10 | 45 | 1%   |
| KP9  | 0.393 | 15 | 4  | 30 | 1.5% |
| KP10 | 0.364 | 16 | 7  | 37 | 0.5% |
| KP12 | 0.322 | 29 | 7  | 30 | 0.5% |
| KP17 | 0.430 | 21 | 7  | 30 | 2%   |
| KP13 | 0.451 | 14 | 7  | 30 | 1%   |
| KP14 | 0.338 | 15 | 7  | 30 | 1%   |
| KP19 | 0.497 | 25 | 7  | 30 | 1%   |
| KP20 | 0.495 | 38 | 10 | 37 | 2%   |

Example 3

Determination of the Optimal Conditions for the Growth of Pure Cultures and the Digest-Prep Consortium In order to determine the optimal conditions for the growth for individual strains of bacteria and the consortium, microorganisms were cultured on medium with CMC in different growth conditions (carboxymethylcellulose substrate concentration, temperature, pH).

To determine the optimum pH, the tested strains of bacteria were passaged onto minimal medium with carboxymethylcellulose, having pH from 4 to 10, respectively. The density of the cultures at the beginning of the experiment was set at approx. $10^6$ cfu/ml. The cultures were incubated for 96 hours at 37° C. The $OD_{600nm}$ value measurements were performed every 24 h.

In order to determine the optimal growth temperature, the tested strains of bacteria were passaged onto minimal medium with carboxymethylcellulose, having pH of 7. The cultures were incubated for 96 h at: 23° C., 30° C., 37° C., 45° C. The $OD_{600nm}$ value measurements were performed every 24 h.

In order to determine the optimal concentration of the substrate carboxymethylcellulose, the tested strains of bacteria were passaged onto minimal medium with 0.5%, 1%, 1.5%, 2% concentration of carboxymethylcellulose (CMC) having pH of 7.0. The cultures were incubated for 96 hours at 37° C. The $OD_{600nm}$ value measurements were performed every 24 h.

In all the tested bacterial strains growth was observed in the above-described ranges of growth conditions, which in fact may somewhat constitute stress factors for these organisms. However, for each strain, different optimum growth conditions were obtained. For most strains, the optimum temperature for growth was about 30° C. and about 37° C. This temperature was higher only for the KP8 strain and it was 45° C. In case of pH of the medium on which the cultures were carried out, the range of the best conditions for growth was from pH 4, for the KP9 strain to pH 10 for the strains: KP4, KP6, KP7, KP8, KP20. The most optimal pH of the medium for most of the strains was 7. As for the concentration of carboxymethylcellulose as the substrate, the range was also quite broad for the isolated bacteria and it ranged between 0.5 and 2% of the CMC concentration. Most of the strains cope very well with the hydrolysis of CMC at high concentrations and prefer such conditions for optimal growth.

The above results may indicate a quite flexible range of optimal conditions, which allow bacterial growth. The obtained results allow to determine the best conditions for growth (temp, 30-37° C.; pH 7-10 and 1-2% CMC concentration) tier the artificially constructed mixtures of strains as well as the Digest-Prep consortium and preparation. Moreover, a broad range of tolerance for external factors allows a mixture of microorganisms to survive even in these extreme and adverse external conditions. The results are shown in Table 2.

Example 4

Construction of the Digest-Prep Consortium and Preparation, and its Component Digest-Prep A, B, C, D, E Mixtures To prepare the Digest-Prep consortium and preparation, smaller mixtures of the Digest-Prep strains A, B, C, D, E, obtained in Example 1., consisting of several different cultures of bacteria were prepared first. The mixtures may comprise the following cultures of bacteria:
  Digest-Prep A: *Bacillus* sp. KP7, KP20; *Ochrobactrum* sp. KP8 (the mixture deposited under the no. B/00064)
  Digest-Prep B: *Providencia* sp. KP14; *Bacillus* sp. KP6, KP16 (the mixture under the no. B/00065)
  Digest-Prep C: *Bacillus* sp. KP4, KP5, KP17, KP22 (the mixture deposited under the no. B/00066)
  Digest-Prep D: *Providencia* sp. KP10; *Bacillus* sp. KP1, KP19 (the mixture deposited under the no. B/00067)
  Digest-Prep E: *Ochrobactrum* sp. KP13; *Bacillus* sp. KP9, KP12 (the mixture deposited under the no. B/00068)

In all the cases, the procedure for preparing components of the mixtures was identical. This procedure is based on obtaining pure cultures of bacteria on a liquid medium with CMC. For this purpose, night culture was cultivated at 30° C. with shaking 120 rpm. After a period of bacterial growth on the medium, the number of cells per ml was determined (fluorescence staining using DAPI dye) and the individual strains were mixed in equal proportions. The density of cells per ml in each of the Digest-Prep mixtures (A, B, C, D, E) was set at $10^7$-$10^8$. The so prepared mixtures of microorganisms were lyophilized for storage purposes and deposited in the Polish Collection of Microorganisms at Lud.wik Hirszfeld Institute of Immunology and Experimental Therapy in Wroclaw.

In order to obtain the cellulolytic Digest-Prep consortium itself all prepared mixtures were mixed together in equal quantitative ratio (so that cell number/ml of each strain of each mixture was equal).

Example 5

Testing for the Presence of Individual Strains in the Digest-Prep Preparation

In order to verify the presence of bacteria in the mixtures of strains constructed in Example 4, isolation of the total DNA of each of the pure cultures according to the method developed by Chen and Kuo in 1993, and isolation of the total DNA in the mixture of strains cultured in LB medium and mixed at a ratio of 1:1 (v/v) was performed. In order to verify the stability of the strains in the consortium growing on a plant substrate, DNA was isolated (using a method developed by Zhou et al., 1996) from cultures on corn silage as the cellulose substrate (concentration of the substrate was 3% of dry weight). On the template of the total isolated DNA, fragments of the 16S rRNA gene were amplified (using the primers specific for the bacteria and according to the method described in Example 1) and then, using the obtained fragment of the 16S rRNA as template, the V3 16S rRNA variable region was amplified. The reaction mixture was prepared according to the instructions of the manufacturer of the Taq DNA Polymerase kit, in a volume of 25 μl. Amplification of DNA of the V3 16S rRNA region was performer using primers 357F and 519R (Muyzer et al., 1993). The PCR products were subjected to qualitative analysis by denaturing gradient gel electrophoresis (DGGE). Separation was carried out in the DCode Universal Mutation Detection (BioRad) system according to the modified method described by Nakatsu et al. (2000). The denaturing factor gradient was in the range from 30 to 55%, whereas a mixture of 7 M urea and 40% formamide constituted 100% solution of the denaturing factor. 6% polyacrylamide gel was used in the electrophoretic separation. Electrophoresis was carried out in ix TAE buffer at 60° C., for 30 minutes at a voltage of 30V, and then at a voltage of 200V for 3.5 hours. After electrophoresis, the gel was stained in SYBR gold solution (1:10 000) and the results of the separation were visualized using the Image Quant software (GE Healthcare). DGGE electrophoresis results indicate bands corresponding to various bacterial genes, characteristic for the individual pure cultures. The results for the individual strains resemble the electrophoretic DNA profile of the constructed consortium, which includes all the strains. DGGE electrophoresis results allowed to roughly estimate and compare the diversity of microorganisms in the consortium. Moreover, the obtained results prove the stability of the individual strains in the mixture. The results are shown in FIG. 1.

Example 6

Degradation of Lignocellulosic Biomass—Corn Silage

To verify what is the real cellulolytic activity of the Digest-Prep preparation constructed in Example 4, tests were carried out using corn silage a substrate which is commonly used in biogas plants world wide. Corn silage is a substrate, the basic component of which is cellulose, which after hydrolysis to simple sugars (glucose) constitutes an assimilable carbon source for most microorganisms. The tests were carried out under conditions reflecting the operation of the industrial hydrolysers from the two-component biogas plants.

Figure 2:
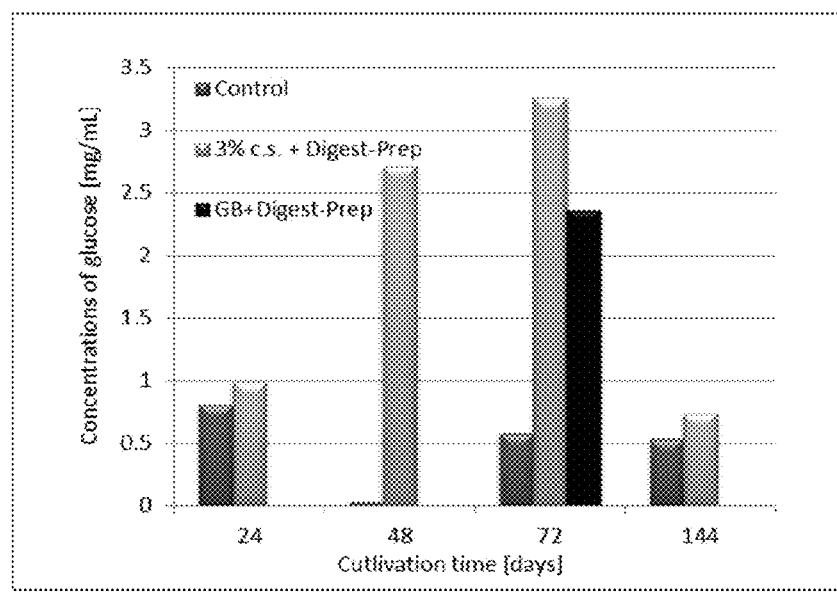
FIG. 2 is a graph showing the effect of hydrolysis of lignocellulosic biomass under the influence of the Digest-Prep preparation (control sample–3% silage without the addition of the Digest-Prep consortium and/or the Digest-Prep preparation; 3% silage+Digest-Prep—culture enriched with the Digest-Prep consortium; 3% silage+GB+Digest-Prep—methanogenic consortium enriched with the Digest-Prep consortium).

The cultures were carried out in a medium containing low-mineralized water with the addition of 3% d.w. of corn silage, under anaerobic conditions at 30° C. for 72 hours. The inoculum (the Digest-Prep preparation, obtained in Example 4), constituted 10% (v/v) of the entire volume of the conducted culture (giving a density of the culture at the level of ~$10^7$ cells/ml). Due to the acidic pH of the corn silage, the initial pH of the culture was increased to 7 using a sodium hydrogencarbonate solution. During the cultivation, samples were taken to determine the pH of the culture, cellulolytic activity of the mixture of strains in the consortium, as well as to determine the changes in the number of bacteria in the consortium mixture and the species composition of the consortium. In order to determine the stability of the strains in the mixture in the culture, DNA isolation and DGGE electrophoresis was performed according to the description in Example 5. The stability of all the 16 strains in the Digest-Prep consortium was confirmed. The results of the cellulolytic activity of the mixture of strains is shown in FIG. 2.

The results of the experiment based on the estimation of the amount of reducing sugars, according to the test with DNS, show that the highest cellulolytic activity of the Digest-Prep preparation occurs after 72 hours of conducting the culture. It is after this incubation period that the highest concentration of glucose in the culture enriched with the cellulolytic consortium was observed. The concentration of glucose in this culture reaches up to 3.25 mg/ml and is 5-times higher than the concentration in the control sample devoid of supplementation with the consortium. With time, the concentration of glucose in the culture decreases. After 144 hours a 4-fold decrease of concentration of glucose is observed, which is probably due to the use of the obtained sugars in the metabolic processes of the strains included in Digest-Prep. The product of cellulose degradation—glucose is also observed in the control sample, probably because bacteria naturally present in corn silage have developed. The concentration level in the control is, however, definitely lower than in the tested sample, and the concentration of sugar decreases in the course of the experiment. Another result presented on the graph is the concentration of glucose during degradation of corn silage in the experiment carried out with methanogenic consortium and the Digest-Prep preparation. The result after 72 hours also illustrates a high concentration of the resulting glucose, which proves the cooperation of the microorganisms included in the methanogenic consortium and the strains of bacteria from the Digest-Prep preparation. The obtained result indicates the possibility of using the Digest-Prep preparation for the degradation of lignocellulosic substrate—corn silage to glucose, in order to provide a source of nutrients for methanogenic microorganisms.

Example 7

The Effect on the Efficiency of Biogas Production-Supporting Methanogens

The main purpose of the Digest-Prep consortium and preparation is to enable the pre-treatment and degradation of lignocellulosic biomass. The products resulting from the hydrolysis of corn silage can be used by other groups of microorganisms in the entire methane fermentation process, having an influence on the level and quality of the obtained biogas. In order to verify the effect of the activity of the consortium on the quality and efficiency of biogas production, an experiment was set with the mixtures: the strains included in the Digest-Prep preparation with the GB methanogenic consortium from the culture collection of the Laboratory of Environmental Pollution Analysis. The following variants of the experiment with the mixtures of the Digest-Prep preparation with the GB methanogenic consortia were performed:

(1) 20% (v/v) of the GB methanogenic consortium with a density of the culture at the level of ~$10^9$ cells/ml (determined using DAPI fluorescence staining and determination by fluorescence microscopy) was mixed with 0% (v/v) mixture of the Digest-Prep strains with a density of the culture at the level of ~$10^8$ cells/ml.

(2) 20% (v/v) of the GB methanogenic consortium (which corresponds to the density of the culture at the level of ~$10^9$ cells/ml) was mixed with 5% (v/v) mixture of the Digest-Prep strains (which corresponds to the density of the culture at the level of ~$10^7$ cells/ml).

(3) 20% (v/v) of the GB methanogenic consortium (which corresponds to the density of the culture at the level of ~$10^9$ cells/nil) without the addition of Digest-Prep, as the control culture.

Figure 3:
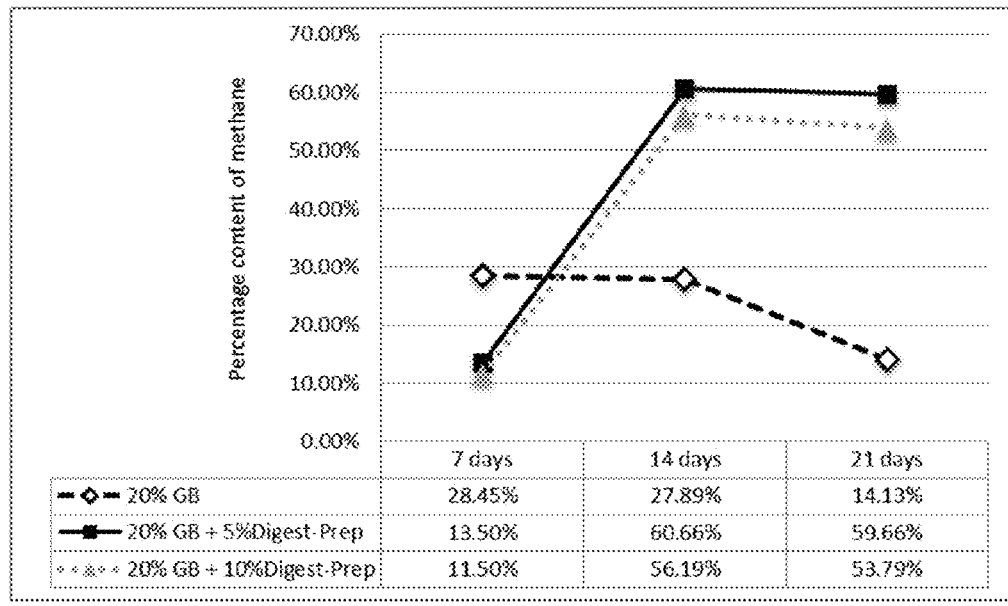
FIG. 3 shows the influence of the activity of the Digest-Prep preparation on biogas production by methanogenic consortium with the use of corn silage as a substrate (GB—methanogenic consortium from the culture collection of the Laboratory of Environmental Pollution Analysis).

The cultures were carried out in glass bioreactors with the active volume of 400 ml using gas bags for measuring the quality of gases. The substrate in the experiment was corn silage at a final concentration of 1% by dry weight. After 72 hours of incubation at 30° C., the temperature of the culture was raised to 37° C. The methane fermentation process was carried out for 21 days, monitoring the volume and quality of the resulting biogas every 7 days. In all the three variants production of biogas was at a similar level (maximally 15 $dm^3$ of biogas/day/kg of d.w. of corn silage) was observed. The observed differences were related to the quality of the produced biogas (FIG. 3.). GC-MS chromatographic analyses showed that the addition of the Digest-Prep preparation influences the improvement of the quality of the produced biogas. The maximum concentration of methane, observed in the control culture was 28.45%, and in the variants with the addition of 10% and 5% (v/v) of the Digest-Prep preparation 56.19% and 60.66% $CH_4$, respectively. These results prove the effectiveness of the Digest-Prep preparation as the "enhancer" of the production of a high-quality biogas. The addition of the Digest-Prep preparation supports the viability and efficiency of methanogenic microorganisms.

Example 8

The Use of the Digest-Prep Preparation for Producing Supplements Necessary in Reviving and Functioning of Methanogens During the degradation of the combined lignocellulosic biomass by cellulolytic bacteria many organic compounds, i.a. volatile fatty acids, simple carbohydrates and many intermediate metabolites are released. These compounds are used by successive groups of microorganisms in the alcoholic or methane fermentation process. In the presented example it was shown that the constructed Digest-Prep consortium/preparation can be used for preparation of supplements of the methane fermentation process. Such supplements can be used in both well-working biogas plants in order to increase the efficiency of the process and increase the rate of the biogas production process by shortening the retention time in the digester, as well as in order to revive the fixed (e.g. frozen of lyophilized) methanogenic microorganisms.

To demonstrate that the Digest-Prep consortium can be used in the production of supplements for methanogenic microorganisms a procedure for preparing and using such formulations was developed. Preparation of the preparations for revival had several steps. The first was a partial degradation of lignocellulosic biomass, namely finning the culture of the Digest-Prep preparation for 72 hours at 30° C. on minimal medium enriched with 3% of d.w. of corn silage at pH 7. After 72 hours of incubation, the entire culture was centrifuged (10 000 rpm, 30 min), culture supernatant was poured into a new vessel and subjected to extraction in an autoclave at 121° C. for 25 minutes, in order to eliminate the remains of microorganisms of the initial culture. The obtained extract (called the Supp-Digest-Prep preparation) was kept at 4° C. until the use in reviving of the methanogenic consortia.

The next step was the enrichment with the Supp-Digest-Prep preparation in a ratio 1:20 of the medium (e.g. 50 ml Supp-Digest-Prep+950 ml of the medium) used for culturing microorganisms, which were to be revived or propagated.

Figure 4:
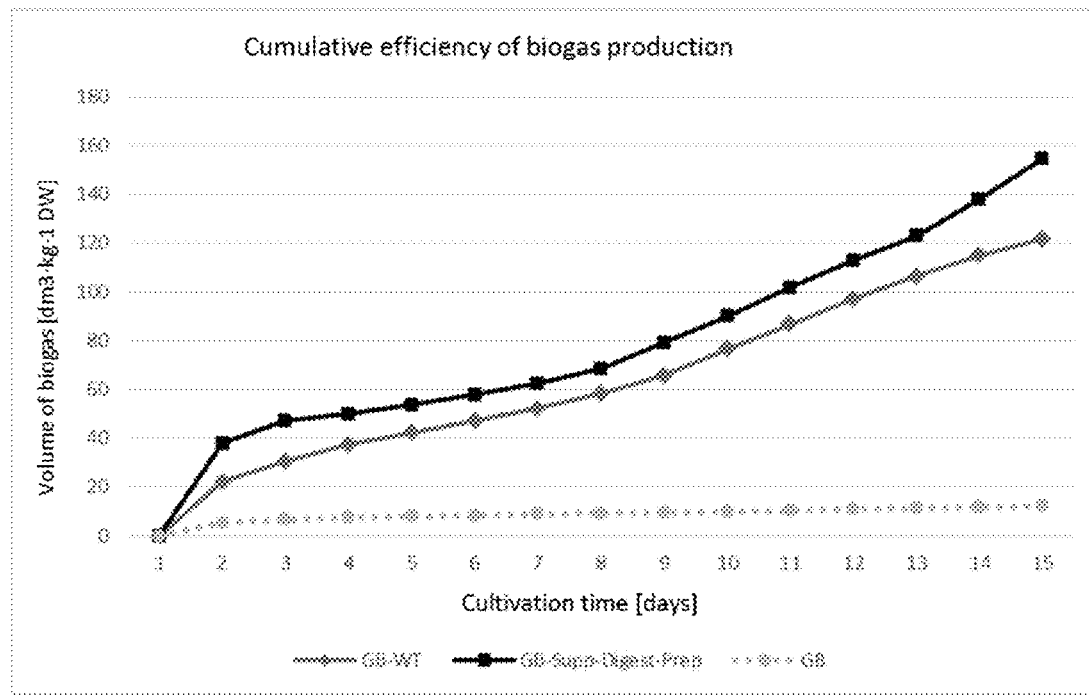
FIG. 4 is a graph showing the cumulative efficiency of biogas production ($dm^3$ $CH_4 \cdot kg^{-1}$ d.w. of corn silage) in the culture of the GB methanogenic consortium before revival, operating in a stable mode (GB-WT) and during revival on minimal medium with the addition of the Supp-Digest-Prep preparation (GB-Supp-Digest-Prep) and without the addition of Supp-Digest-Prep (GB).

In order to verify the effectiveness of the Supp-Digest-Prep preparation, revival of a consortium of methanogenic microorganisms was performed in two variants: (i) control—without the enrichment of the culture with the Supp-Digest-Prep preparation and (ii) basic—with the addition of the Supp-Digest-Prep preparation. For revival, consortia of methanogenic microorganisms labeled as GB in the culture collection of the Laboratory of Environmental Pollution Analysis were used. The methanogenic consortia were kept at −70° C. in the mixture of 10% glycerol and 10% DMSO. In order to revive the consortia, they were gradually thawed at 4° C., and then cultures were started in laboratory reactors with a final volume of 900 ml. As the substrate 1% of d.w. of shredded corn silage was used, and 0.1% yeast extract was added as an additional source of carbon. The cultures were supplemented with a mixture of vitamins 10 ml/l and Touvinen's salts 2 ml/l. In the basic variant, the cultures were supplemented with 50 ml/l of the Supp-Digest-Prep preparation, and in the control variant—without the enrichment with the Supp-Digest-Prep preparation. The cultures were started under anaerobic conditions in an anaerobic chamber and were carried out for 14/21 days. During culture, the increase in the volume of the produced biogas was monitored. In the control variant, without the addition of the Supp-Digest-Prep preparation, trace biogas production (at the level of 0.8 $dm^3$/day/kg of d.w. of corn silage) was observed, while in the basic variant revival of the consortium of methanogenic microorganisms and biogas production was reported (FIG. 4). The efficiency of biogas production in the revived methanogenic consortium was maximally ~11 $dm^3$ biogas/day/1 kg of d.w. of corn silage, and in the stabilized methanogenic consortium working before freezing, the efficiency was ~8 $dm^3$ biogas/day/1 kg of d.w. of corn silage. The obtained results indicate that the use of the Supp-Digest-Prep preparation affects the revival and promotes viability and efficiency of the consortium of methanogenic microorganisms.

Example 9

The Influence of the Supp-Digest-Prep-Plus Combination Preparation on the Quality and Efficiency of Biogas Produced in Methane Fermentation Due to the constructed Digest-Prep consortium and preparation and the Supp-Digest-Prep preparation it is possible to affect various stages of the methane fermentation process. Both at the hydrolysis step, with the use of the Digest-Prep consortium and/or preparation, and during methanogenesis, by providing the produced supplements, contained in the Supp-Digest-Prep preparation, to methanogenic microorganisms.

In order to investigate the combined effect of the Digest-Prep consortium/preparation combined with the Supp-Digest-Prep preparation, methane fermentation process was carried out using methanogenic consortia (GB—from the culture collection of the Laboratory of Environmental Pollution Analysis) in the following variants: (i) control (GB-WT) without the addition of preparations to the culture, (ii) GB+i-Digest-Prep—with the addition of the Digest-Prep preparation, (iii) GB+Supp-Digest-Prep-Plus culture enriched with both the Digest-Prep preparation and the supplements of Supp-Digest-Prep. The cultures were carried out in laboratory reactors with a final volume of 900 ml.

As the substrate, 1% d.w. of shredded corn silage was used. The cultures were supplemented with a mixture of vitamins 10 ml/l and Touvinen's salts 2 ml/l. In all the variants, 75% (v/v) GB methanogenic consortium was used. In the variant with the Digest-Prep preparation, the cultures were enriched with 10% and 5% (v/v) Digest-Prep preparation, respectively. In the variant with the combined Supp-Digest-Prep-Plus preparation, 10% (v/v) preparation and 10% Supp-Digest-Prep were used. The cultures were started under anaerobic conditions in an anaerobic chamber and were carried for 14 days. During culture, the volume of the produced biogas and methane content in the biogas were monitored by GC-MS chromatographic analyses.

Figure 5:
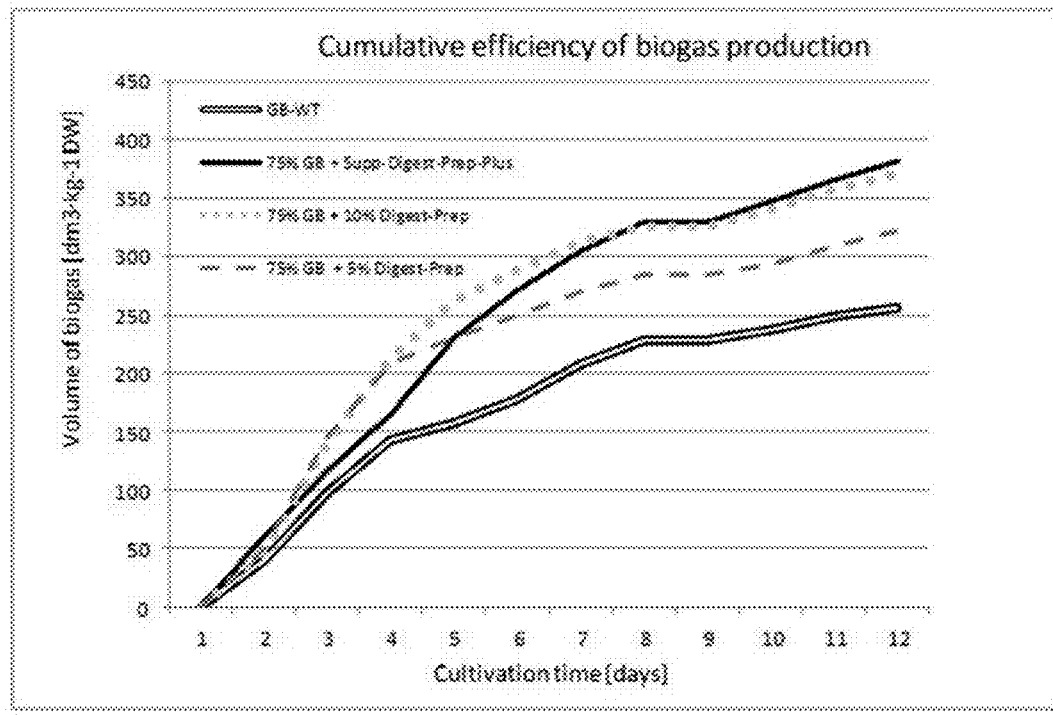
FIG. 5 is a graph showing the cumulative efficiency of biogas production ($dm^3$ $CH_4 \cdot kg^{-1}$ d.w. of corn silage) in the culture of the GB methanogenic consortium working without the addition of the Digest-Prep preparation, Supp-Digest-Prep, with the addition of the Digest-Prep preparation only, and with the addition of the Supp-Digest-Prep-Plus combined preparation (the Digest-Prep preparation in combination with Supp-Digest-Prep).
Figure 6:
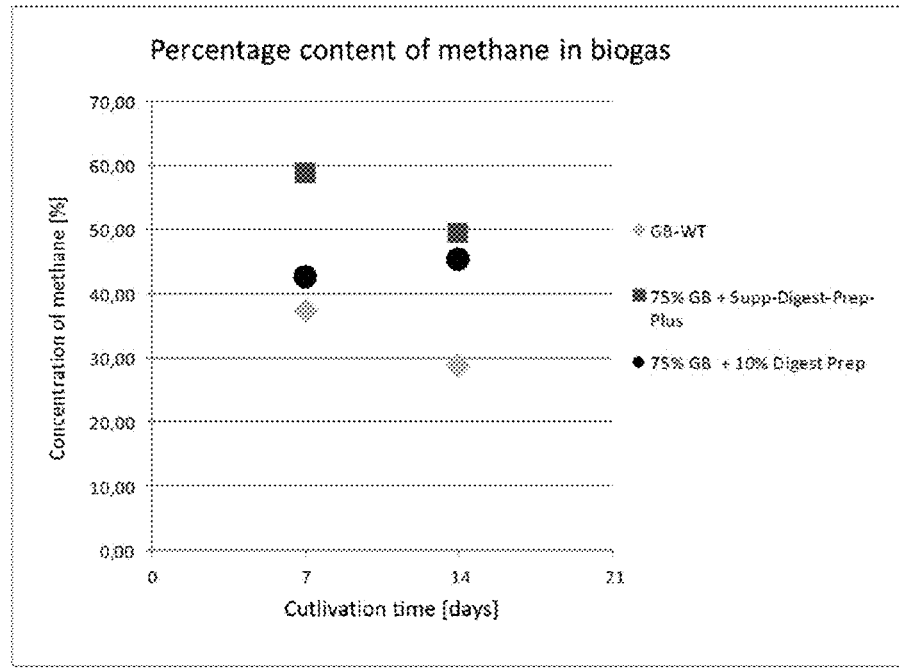
FIG. 6 is a graph showing the effect of the activity of the Digest-Prep preparation and the synergistic effect of the Supp-Digest-Prep-Plus combined preparation (the Digest-Prep preparation in combination with Supp-Digest-Prep) on the percentage content of methane in the obtained biogas in the culture with methanogenic consortium (GB—from the culture collection of the Laboratory of Environmental Pollution Analysis).

In all the variants differences in the amount of the produced biogas were observed (FIG. 5). In the control variant, biogas production at the level of 15-18 dm³/day/kg of d.w. of corn silage was observed. In the variant with the addition of the Digest-Prep preparation and the addition of the Supp-Digest-Prep-Plus combination preparation, biogas production at the level of 30-35 dm³/day/kg of d.w. of corn silage was reported. The GC-MC chromatographic analyses supplemented the results concerning the quality of the produced biogas (FIG. 6). The maximum concentration of methane in the control culture was 37%, in the culture with the Digest-Prep preparation 40-45%, and in the culture with the Supp-Digest-Prep-Plus combination preparation, it reached up to 58%. The obtained results indicate an unexpected synergistic effect of the preparation on the methane fermentation process. The results indicate the enhanced effectiveness of the combined effect of these preparations. As a result, the use of such a combination preparation enables and facilitates the production of a high quality biogas.

LITERATURE

Bushnell D. L. i Haas H. F., 1941. The utilization of certain hydrocarbon by microorganisms; Kansas Agricultural Experiment Station, 199: 653-673.

Chen W. P. i Kuok T. T. 1993. A simple Rapid method for the preparation of gram-negative bacterial genomic DNA, Nucleic Acids Res. 21: 2260.

Gathogo E. W., Waugh A. C., Peril N., Red path M. B., Long P. F., 2003. Colony PCR amplification of actinomycetes DNA. J. Antibiot. 56: 423-424.

Chose T. K. 1987. Measurement of cellulase activities. Pure Appl Chem 59: 257-268.

Hendricks C. W., Doyle J. D., Hugley B, 1995. A new solid medium for enumerating cellulose-utilizing bacteria in soil; Applied and Environmental Microbiology, 61: 2016-2019.

Lane D. J., 16S/23S rRNA sequencing. 1991. (Stackebrandt E., Goodfellow M., red.) Nucleic Acid Techniques in Bacterial Systematics John Wiley and Sons: New York Muyzer G., Waal de E. C. Uitterlinden A. G., 1993. Profiling of combined microbial populations by denaturing gradient gel electrophoresis analysis of polymerase chain reaction-amplified genes coding for 16S rRNA. Appl. Environ, Microbiol. 59: 695-700

```
SEQUENCE LISTING
<110> University of Warsaw

<120> Consortium and a preparation of microorganisms for catalyzing
cellulose hydrolysis, preparation for methane fermentation supplementation,
combination preparation, use thereof and method using the same

<130> PK/2509/AGR

<160> 16

<170> PatentIn version 3.5

<210> 1

<211> 1525

<212> DNA

<213> Bacillus licheniformis

<400> 1
gattagagtt tgatcctggc tcaggacgaa cgctggcggc gtgcctaata catgcaagtc      60
gagcggaccg acgggagctt gctcccttag gtcagcggcg gacgggtgag taacacgtgg     120
gtaacctgcc tgtaagactg ggataactcc gggaaaccgg ggctaatacc ggatgcttga     180
ttgaaccgca tggttcaatt ataaaggtg gcttttagct accacttaca gatggacccg      240
cggcgcatta gctagttggt gaggtaacgg ctcaccaagg caacgatgcg tagccgacct     300
gagagggtga tcggccacac tgggactgag acacggccca gactcctacg ggaggcagca     360
gtagggaatc ttccgcaatg gacgaaagtc tgacggagca acgccgcgtg agtgatgaag     420
gttttcggat cgtaaaactc tgttgttagg gaagaacaag taccgttcga atagggcggt     480
accttgacgg tacctaacca gaaagccacg gctaactacg tgccagcagc cgcggtaata     540
cgtaggtggc aagcgttgtc cggaattatt gggcgtaaag cgcgcgcagg cggtttctta     600
agtctgatgt gaaagccccc ggctcaaccg gggagggtca ttggaaactg gggaacttga     660
```

```
gtgcagaaga ggagagtgga attccacgtg tagcggtgaa atgcgtagag atgtggagga        720
acaccagtgg cgaagcgact ctctggtctg taactgacgc tgaggcgcga aagcgtgggg        780
agcgaacagg attagatacc ctggtagtcc acgccgtaaa cgatgagtgc taagtgttag        840
agggtttccg ccctttagtg ctgcagcaaa cgcattaagc actccgcctg ggagtacgg         900
tcgcaagact gaaactcaaa ggaattgacg ggggcccgca caagcggtgg agcatgtggc        960
ttaattcgaa gcaacgcgaa gaaccttacc aggtcttgac atcctctgac aaccctagag       1020
atagggcttc cccttcgggg gcagagtgac aggtggtgca tggttgtcgt cagctcgtgt       1080
cgtgagatgt tgggttaagt cccgcaacga gcgcaaccct tgatcttagt tgccagcatt       1140
cagttgggca ctctaaggtg actgccggtg acaaaccgga ggaaggtggg gatggcgtca       1200
aatcatcatg cccctatga cctgggctac acacgtgcta caatgggcag aacaaagggc        1260
agcgaagccg cgaggctaag ccaatcccac aaatctgttc tcagttcgga tcgcagtctg       1320
caactcgact gcgtgaagct ggaatcgcta gtaatcgcgg atcagcatgc cgcggtgaat       1380
acgttcccgg gccttgtaca caccgcccgt cacaccacga gagtttgtaa cacccgaagt       1440
cggtgaggta acctttagg agccagccgc cgaaggtggg acagatgatt ggggtgaagt        1500
cgtaacaagg taaccaatca ctagt                                             1525
<210> 2
<211> 1635
<212> DNA
<213> Bacillus pumilus
<400> 2
gcgtgtcaac ttcctattgg gggcggagtt gggacgacgt cgcatgctcc cggccggatt         60
agagtttgat cctggctcag gacgaacgct ggcggcgtgc ctaatacatg caagtcgagc        120
gaacagaagg gagcttgctc ccggatgtta gcggcggacg ggtgagtaac acgtgggtaa        180
cctgcctgta agactgggat aactccggga aaccggagct aataccggat agttccttga        240
accgcatggt ccaaggatga agacggtttc ggctgtcac ttacagatgg acccgcggcg         300
cattagctag ttggtggggt aatggctcac caaggcgacg atgcgtagcc gacctgagag        360
ggtgatcggc cacactgggg ctgagacacg gcccagactc ctacgggagg cagcagtagg        420
gaatcttccg caatggacga aagtctgacg gagcaacgcc gcgtgagtga tgattgtttt        480
cggatcccaa agctctgttg ttagggaaga acaagaggga gaggagctgc tcgcaccttg       540
acggtacgta accagaaagc cacggctaac tacgtgccag ctgccgcggt aatacgtagg       600
tggcaagcgt tgtccgggat tattgggcgt aaagggctcg caggcggttt cttaagtctg       660
atgtgaaagc ccccggctca accggggagg gtcattggag actgggaaac ttgagtgcag        720
aagaggagag tggaattcca cgtgtagcgg tgaaatgctt agagatgtgg aggaacacca       780
gtggcgaatg cgactctctg gtctgtaact gacgctgagg agcgaaagcg tggggagcga       840
caggattaga taccctggta gtccacgccg taaacgatga gtgctaagtg ttaggggggt       900
ttccgccect tagtgctgca gctaacgcat taagcactcc gcctgggag tacggtcgca        960
agactgaaac tcaaaggaat tgacggggc ccgcacaagc ggtggagcat gtggtttaat       1020
tcgaagcaac gcgaagaacc ttaccaggtc ttgacatcct ctgacaaccc tagagatagg      1080
gctttccctt cggggacaga gtgacaggtg gtgcatgcca gtcgtcagct cgtgtcgcga      1140
catgttgggt taagtcccgc aacgagcgca gcccttgatc ttagttgcca gcatttagtt      1200
```

-continued

```
gggcactcta aggtgactgc cggtgacaaa ccggaggaag gtggggatga cgtcaaatca      1260
tcatgcccct tatgacctgg gctacacacg tgctacaatg gacagaacaa agggttgcga      1320
gaccgcaagg tttagccaat cccataaatc tgttctcagt tcggatcgca gtctgcaact      1380
cgactgcgtg aagctggaat cgctagtaat cgcggatcag catgccgcgg tgaatacgtt      1440
cccgggcctt gtacacaccg cccgtcacac cacgagagtt tgtaacaccc gaagtcggtg      1500
aggtaacctt tatggagcca gccgccgaag gtgggacaga tgattggggt gaagtcgtaa      1560
caaggtaacc aatcactagt cgcgttggat gcatagcttg agtattctaa tacggtcacc      1620
aaaattacct tgtta                                                       1635
```

<210> 3
<211> 1620
<212> DNA
<213> *Bacillus pumilus*

<400> 3

```
ctatagggcg attgggcccg acgtcgcatg ctcccggccg gattagagtt tgatcctggc       60
tcaggacgaa cgctggcggc gtgcctaata catgcaagtc gagcgaacag aagggagctt      120
gctcccggat gttagcggcg gacgggtgag taacacgtgg gtaacctgcc tgtaagactg      180
ggataactcc gggaaaccgg agctaatacc ggatagttcc ttgaaccgca tggttcaagg      240
gtgaaagacg gtttcggctg tcacttacag atggacccgc ggcgcattag ctagttggtg      300
gggtaatggc tcaccaaggc gacgatgcgt agccgacctg agagggtgat cggccacact      360
gggactgaga cacggcccag actcctacgg gaggcagcag tagggaatct tccgcaatgg      420
acgaaagtct gacggagcaa cgccgcgtga gtgatgaagg ttttcggatc gtaaagctct      480
gttgttaggg aagaacaagt gcgagagtaa ctgctcgcac cttgacgtgg cctaaccaga      540
aagccacggc tagctacgtg ccagcagccg cggtaatacg taggtggcaa gcgttgtccg      600
gaattattgg gcgtaaaggg ctcgcaggcg gtttcttaag gtctgatgtg aaagcccccg      660
gctcaaccgg ggagggtcat tggaaactgg gaaacttgag tgcagaagag gagagtggaa      720
ttccacgtgt agcggtgaaa tgcgtagaga tgtggaggaa caccagtggc gaaggcgact      780
ctctggtctg taactgacgc tgaggagcga aagcgtgggg agcgaacagg attagatacc      840
ctggtagtca cgccgtaaac gatgagtgct aagtgtttgg gggtttccgc ccccttagtg      900
ctgcagctaa cgcattaagc actccgcctg gggagtacgg tcgcaagact gaaactcaaa      960
ggaattgacg ggggcccgca caagcggtgg agcatgtggt ttaattcgaa gcaacgcgaa     1020
gatccttgtc aggtcttgac atcctctgac aaccctagag acagggcttt cccttcgggg     1080
acagagtgac aggtggtgcc atggttgtcg tcagctcgtg tcgtgagatg ttgggttaag     1140
tcccgcaacg agcgcaaccc ttgatgttag ttgccagcat ttagttgggc actctaaggt     1200
gactgccggt gacaaaccgg aggaaggtgg ggatgacgtc aaatcatcat gccccttatg     1260
acctgggcta cacacgtgct acaatggaca gaacaaaggg ctgcgagacc gcaaggttta     1320
gccaatccca taaatctgtt ctcagttcgg atcgcagtct gcaactcgac tgcgtgaagc     1380
tggaatcgct agtaatcgcg gatcagtatg ccgcggtgaa tacgttcccg ggccttgtac     1440
acaccgcccg tcacaccacg agagtttgta acacccgaag tcggtgaggt aacctttatg     1500
gagccagccg ccgaaggtgg gacagatgat tggggtgaag tcgtaacaag gtaaccaatc     1560
actagtaacg cgttggatgc atagcttgag tattctatag ttcacccaaa aaaggcccc     1620
```

<210> 4

<211> 1527

<212> DNA

<213> Bacillus pumilus

<400> 4

```
gattaccagt tgatcctgg ctcaggacga acgctggcgg cgtgcctaat acatgcaagt      60
cgagcggaca aagggagct tgctcccgga tgttagcggc ggacgggtga gtaacacgtg     120
ggtaacctgc ctgtaagact gggataactc cgggaaaccg gagctaatac cggatagttc    180
cttgaaccgc atggttcaag gatgaaagac ggtttcggct gtcacttaca gatggacccg    240
cggcgcatta gctagttggt ggggtaatgg ctcaccaagg cgacgatgcg tagccgacct    300
gagagggtga tcggccacac tgggactgag acacggccca gactcctacg ggaggcagca    360
gtagggaatc ttccgcaatg gacgaaagtc tgacggagca acgccgcgtg agtgatgaag    420
gttttcggat cgtaaagctc tgttgttagg gaagaacaag tgcgagagta actactcgca    480
ccttgacggt acctaaccag aaagccacgg ctaactacgt gccagcagcc gcggtaatac    540
gtaggtggca agcgttgtcc ggaattattg ggcgtaaagg ctcgcaggc ggtttcttaa     600
gtctgatgtg aaagcccccg gctcaaccgg ggagggtcat tggaaactgg gaaacttgag    660
ttgcagaaga ggagagtgga attccacgtg tagcggtgaa atgcgtagag atgtggagga    720
acaccagtgg cgaaggcgac tctctggtct gtaaactgac gctgaggagc gaaagcgtgg    780
ggagcgaaca ggattagata ccctggtagt ccacgccgta acgatgagt gctaagtgtt     840
agggggtttc cgccccttag tgctgcagct aacgcattaa gcactccgcc tggggagtac    900
ggtcgcaaga ctgaaactca aaggaattga cggggcccg cacaagcggt ggagcatgtg     960
gtttaattcg aagcaacgcg aagaaccta ccaggtcttg acatcctctg acaaccctag    1020
agataggggct ttcccttcgg ggacagagtg acaggtggtg catggttgtc gtcagctcgt   1080
gtcgtgagat gttgggttaa gtcccgcaac gagcgcaacc cttgatctta gttgccagca   1140
tttagttggg cactctaagg tgactgccgg tgacaaaccg gaggaaggtg gggatgacgt    1200
caaatcatca tgcccttat gacctgggct acacacgtgc tacaatggac agaacaaagg    1260
gctgcgagac cgcaaggttt agccaatccc ataaatctgt tctcagttcg gatcgcagtc    1320
tgcaactcga ctgcgtgaag ctggaatcgc tagtaatcgc ggatcagcat gccgcggtga   1380
atacgttccc gggccttgta cacaccgccc gtcacaccac gagagtttgc aacacccgaa    1440
gtcggtgagg taaccttat ggagccagcc gccgaaggtg gggcagatga ttggggtgaa     1500
gtcgtaacaa ggtaaccaat cactagt                                        1527
```

<210> 5

<211> 1408

<212> DNA

<213> Bacillus altitudinis

<400> 5

```
aaggtaacca agtagagttt gatcctggct cattaagtcg taacaaggta accaagtaga     60
gtttgatcct ggcgcaaacc gtcgcaacaa gggacccgtt ccttgaaccg catggttcaa    120
ggatgaaaga cggtttcggc tgtcacttac agatggaccc gcggcgcatt agctagttgg    180
tgaggtaacg gctcaccaag cgacgatgc gtagccgacc tgagagggtg atcgccaca     240
ctgggactga gacacggccc acactcctac gggaggcagc agtagggaat cttccgcaat    300
```

-continued

| | |
|---|---|
| ggacgaaagt ctgacggagc aacgccgcgt gagtgatgaa ggttttcgga tcgtaaagct | 360 |
| ctgttgttag ggaagaacaa gtgcaagagt aactgcttgc accttgacgg tacctaacca | 420 |
| gaaagccacg gctaactacg tgccagcagc cgcggtaata cgtaggtggc aagcgttgtc | 480 |
| cggaattatt gggcgtaaag ggctcgcagg cggtttctta agtctgatgt gaaagccccc | 540 |
| ggctcaaccg ggagggtca ttggaaactg ggaaacttga gtgcagaaga ggagagtgga | 600 |
| attccacgtg tagcggtgaa atgcgtagag atgtggagga acaccagtgg cgaaggcgac | 660 |
| tctctggtct gtaactgacg ctgaggagcg aaagcgtggg gagcgaacag gattagatac | 720 |
| cctggtagtc cacgccgtaa acgatgagtg ctaagtgtta gggggtttcc gcccttagt | 780 |
| gctgcagcta acgcattaag cactccgcct ggggagtacg gtcgcaagac tgaaactcaa | 840 |
| aggaattgac gggggcccgc acaagcggtg gagcatgtgg tttaattcga agcaacgcga | 900 |
| agaaccttac caggtcttga catcctctga caaccctaga gatagggctt tcccttcggg | 960 |
| gacagagtga caggtggtgc atggttgtcg tcagctcgtg tcgtgagatg ttgggttaag | 1020 |
| tcccgcaacg agcgcaaccc ttgatcttag ttgccagcat tcagttgggc actctaaggt | 1080 |
| gactgccggt gacaaaccgg aggaaggtgg ggatgacgtc aaatcatcat gccccttatg | 1140 |
| acctgggcta cacacgtgct acaatggaca gaacaaaggg ctgcgagacc gcaaggttta | 1200 |
| gccaatccca caaatctgtt ctcagtgatc atggctgtgt aagtcgtaac aaggtaacca | 1260 |
| agtagagttt gatcctggct cagtaagttg taacaaggta accaagtaga gtttgatcct | 1320 |
| ggctcagtaa gtcgtaacaa ggtaaccaag tagagtttga tcctggctca gtaagtcgga | 1380 |
| acaaaggaac caacttgggt tgtctgcg | 1408 |

<210> 6

<211> 1459

<212> DNA

<213> Orchrobactrum sp

<400> 6

| | |
|---|---|
| gattagagtt tgatcatggc tcagaacgaa cgctggcggc aggcttaaca catgcaagtc | 60 |
| gaacggtctc ttcggaggca gtggcagacg ggtgagtaat gcatgggaat ctaccattct | 120 |
| ctacggaata actcagggaa acttgtgcta ataccgtata cgccttttg gggaaagatt | 180 |
| tatcggagag tgatgagccc atgttggatt agctagttgg tggggtaaag gcctaccaag | 240 |
| gcgacgatcc atagctggtc tgagaggatg atcagccaca ctgggactga gacacggccc | 300 |
| agactcctac gggaggcagc agtggggaat attggacaat gggcgcaagc ctgatccagc | 360 |
| catgccgcgt gagtgatgaa ggtcttagga ttgtaaagct ctttcaccgg tgaagataat | 420 |
| gacggtaacc ggagaagaag ccccggctaa cttcgtgcca gcagccgcgg taatacgaag | 480 |
| ggggctagcg ttgttcggat ttactgggcg taaagcgcac gtaggcggac ttttaagtca | 540 |
| ggggtgaaat cccagagctc aactctggaa ctgcctttga tactggaagt cttgagtatg | 600 |
| gaagaggtga gtggaattcc gagtgtagag gtgaaattcg tagatattcg gaggaacacc | 660 |
| agtggcgaag gcggctcact ggtccattac tgacgctgag gtgcgaaagc gtgggagca | 720 |
| aacaggatta gataccctgg tagtccacgc cgtaaacgat gaatgttagc cgtcggggtg | 780 |
| tttacacttc ggtggcgcag ctaacgcatt aaacattccg cctggggagt acggtcgcaa | 840 |
| gattaaaact caaaggaatt gacggggggcc cgcacaagcg gtggagcatg tggtttaatt | 900 |
| cgaagcaacg cgcagaacct taccagccct tgacataccg gtcgcggaca cagagatgtg | 960 |
| tctttcagtt cggctggacc ggatacaggt gctgcatggc tgtcgtcagc tcgtgtcgtg | 1020 |

-continued

```
agatgttggg ttaagtcccg caacgagcgc aaccctcgcc tttagttgcc atcatttggt    1080
tgggcactct aaagggactg ccagtgataa gctggaggaa ggtggggatg acgtcaagtc    1140
ctcatggccc ttacgggctg ggctacacac gtgctacaat ggtggtgaca gtgggcagca    1200
agcgtgcgag cgcaagctaa tctccaaaag ccatctcagt tcggattgca ctctgcaact    1260
cgagtgcatg aagttggaat cgctagtaat cgcggatcag catgccgcgg tgaatacgtt    1320
cccgggcctt gtacacaccg cccgtcacac catgggagtt ggttctgccc gaaggcactg    1380
tgctaaccgt aaggaggcag gtgaccacgg tagggtcagc gactggggtg aagtcgtaac    1440
aaggtaacca atcactagt                                                 1459
```

<210> 7

<211> 1526

<212> DNA

<213> *Bacillus sp.*

<400> 7

```
gattagagtt tgatcctggc tcaggacgaa cgctggcggc gtgcctaata catgcaagtc     60
gagcggacag aagggagctt gctcccggat gttagcggcg gacgggtgag taacacgtgg    120
gtaacctgcc tgtaagactg ggataactcc gggaaaccgg agctaatacc ggatagttcc    180
ttgaaccgca tggttcaagg atgaaagacg gtttcggctg tcacttacag atggacccgc    240
ggcgcattag ctagttggtg aggtaacggc tcaccaaggc gacgatgcgt agccgacctg    300
agagggtgat cggccacact gggactgaga cacggcccag actcctacgg gaggcagcag    360
tagggaatct tccgcaatgg acgaaagtct gacggagcaa cgccgcgtga gtgatgaagg    420
ttttcggatc gtaaagctct gttgttaggg aagaacaagt gcaagagtaa ctgcttgcac    480
cttgacggta cctaaccaga aagccacggc taactacgtg ccagcagccg cggtaatacg    540
taggtggcaa gcgttgtccg gaattattgg gcgtaaaggg ctcgcaggcg gtttcttaag    600
tctgatgtga aagcccccgg ctcaaccggg gagggtcatt ggaaactggg aaacttgagt    660
gcagaagagg gagagtggaa ttccacgtgt agcggtgaaa tgcgtagaga tgtggaggaa    720
caccagtggc gaaggcgact ctctggtctg taactgacgc tgaggagcga aagcgtgggg    780
agcgaacagg attagatacc ctggtagtcc acgccgtaaa cgatgagtgc taagtgttag    840
ggggtttccc gccccttagt gctgcagcta acgcattaag cactccgcct ggggagtacg    900
gtcgcaagac tgaaactcaa aggaattgac ggggcccgc acaagcggtg aagcatgtgg    960
tttaattcga agcaacgcga agaaccttac caggtcttga catcctctga caacctaga    1020
gatagggctt tccttcgggg acagagtga caggtggtgc atggttgtcg tcagctcgtg    1080
tcgtgagatg ttgggttaag tcccgcaacg agcgcaaccc ttgatcttag ttgccagcat    1140
tcagttgggc actctaaggt gactgccggt gacaaaccgg aggaaggtgg ggatgacgtc    1200
aaatcatcat gccccttatg acctgggcta cacacgtgct acaatggaca gaacaaaggg    1260
ttgcgagacc gcaaggttta gccaatccca caaatctgtt ctcagttcgg atcgcagtct    1320
gcaactcgac tgcgtgaagc tggaatcgct agtaatcgcg gatcagcatg ccgcggtgaa    1380
tacgttcccg ggccttgtac acaccgcccg tcacaccacg agagtttgca acacccgaag    1440
tcggtgaggt aacctttatg gagccagccg ccgaaggtgg ggcagatgat tggggtgaag    1500
tcgtaacaag gtaaccaatc actagt                                        1526
```

<210> 8

<211> 1518

<212> DNA

<213> Providencia vermicola

<400> 8

| gattagagtt tgatcatggc tcagattgaa cgctggcggc aggcctaaca catgcaagtc | 60 |
| --- | --- |
| gagcggtaac aggggaagct tgcttcccgc tgacgagcgg cggacgggtg agtaatgtat | 120 |
| ggggatctgc ccgatagagg gggataacca ctggaaacgg tggctaatac cgcataatct | 180 |
| ctcaggagca aagcagggga acttcggtcc ttgcgctatc ggatgaaccc atatgggatt | 240 |
| agctagtagg tgaggtaatg gctcacctgg gcgacgatcc ctagctggtc tgagaggatg | 300 |
| atcagccaca ctgggactga gacacggccc agactcctac gggaggcagc agtggggaat | 360 |
| attgcacaat gggcgcaagc ctgatgcagc catgccgcgt gtatgaagaa ggccctaggg | 420 |
| ttgtaaagta cttcagtcg ggaggaaggc gttgatgcta atatcatcaa cgattgacgt | 480 |
| tatcgacaga agaagcaccg gctaactccg tgccagcagc cgcggtaata cggagggtgc | 540 |
| aagcgttaat cggaattact gggcgtaaag cgcacgcagg cggttgatta agttagatgt | 600 |
| gaaatccccg gcttaacct gggaatggca tctaagactg gtcagctaga gtcttgtaga | 660 |
| ggggggtaga attccatgtg tagcggtgaa atgcgtagag atgtggagga ttacccggtg | 720 |
| gcgaaggcg gccccctgga caaagactga cgctcaggtg cgaaagcgtg gggagcaaac | 780 |
| aggattagat accctggtag tccacgctgt aaacgatgtc gatttgaagg ttgttcccct | 840 |
| gaggagtggc ttttcggagc taacgcgtta atcgaccgc ctggggagta cggccgcaag | 900 |
| gttaaaactc aaatgaattg acgggggccc gcacaagcgg tggagcatgt ggtttaattc | 960 |
| gatgcaacgc gaagaaccct tacctactctt gacatccaga gaacttagca gagatgcttt | 1020 |
| ggtgccttcg ggaactctga acaggtgct gcatggctgc cgtcagctcg tgttgtgaaa | 1080 |
| tgttgggtta gtcccgcaa cgagcgcaac ccttatcctt tgttgccagc gattcggtcg | 1140 |
| ggaactcaaa ggagactgcc ggtgataaac cggaggaagg tggggatgac gtcaagtcat | 1200 |
| catgcccctt acgagtaggg ctacacacgt gctacaatgg cgtatacaaa gagaagcgac | 1260 |
| ctcgcgaggg caagcggaac tcataaagla cgtcgtagtc cggattggag tctgcaactc | 1320 |
| gactccatga gtcggaatc gctagtaatc gtagatcaga atgctacggt gaatacgttc | 1380 |
| ccgggccttg tacacaccgc ccgtcacacc atgggagtgg gttgcaaaag aagtaggtag | 1440 |
| cttaacctgc ggagggcgc ttaccacttt gtgattcatg actggggtga agtcgtaaca | 1500 |
| aggtaaccaa tcactagt | 1518 |

<210> 9

<211> 1526

<212> DNA

<213> Bacillus sp.

<400> 9

| gattagagtt tgatcatggc tcaggacgaa cgctggcggc gtgcctaata catgcaagtc | 60 |
| --- | --- |
| gagcggacag aagggagctt gctcccggat gttagcggcg gacgggtgag taacacgtgg | 120 |
| gtaacctgcc tgtaagactg ggataactcc gggaaaccgg agctaatacc ggaaagttcc | 180 |
| ttgaaccgca tggttcaagg atgaaagacg gtttcggctg tcacttacag atggacccgc | 240 |
| ggcgcattag ctagttggtg gggtaatggc tcaccaaggc gacgatgcgt agccgacctg | 300 |
| agagggtggt cggccacact gggactgaga cacgcccag actcctacgg gaggcagcag | 360 |

```
tagggaatct tccgcaatgg acgaaagtct gacggagcaa cgccgcgtga gtgatgaagg      420
ttttcggatc gtaaagctct gttgttaggg aagaacaagt gcgagagtaa ctactcgcac      480
cttgacggta cctaaccaga aagccacggc taactacgtg ccagcagccg cggtaatacg      540
taggtggcaa gcgttgtccg gaattattgg gcgtaaaggg ctcgcaggcg gtttcttaag      600
tctgatgtga agcccccggg ctcaaccggg gagggtcatt ggaaactggg aaacttgagt      660
gcagaagagg agagtgggat tccacgtgta gcggtgaaat gcgtagagat gtggaggggaa     720 caccagtggc gaaggcgact ctctggtctg taactgacgc tgaggagcga aagcgtgggg      780
agcgaacagg attagatacc ctggtagtcc acgccgtaaa cgatgagtgc taagtgttag      840
ggggtttccg ccccttagtg ctgcagctaa cgcattaagc actccgcctg ggagtacgg       900 tcgcaagact gaaactcaaa ggaattgacg ggggcccgca caagcggtgg agcatgtggt      960
ttaattcgaa gcaacgcgaa gaaccttacc aggtcttgac atcctctgac aaccctagag     1020
atagggcttt cccttcgggg acagagtgac aggtggtgca tggttgtcgt cagctcgtgt     1080
cgtgagatgt tgggttaagt cccgcaacga gcgcaacccc tgatcttagt tgccagcatt    1140
tagttgggca ctctaaggtg actgccggtg acaaaccgga ggaaggtggg gatgacgtca     1200
aatcatcatg ccccttatga cctgggctac acacgtgcta cagtggacag aacaaagggc    1260
tgcgagaccg caaggtttag ccaatcccat gaatctgttc tcagttcgga tcgcagtctg     1320
caactcgact gcgtgaagct ggaatcgcta gtaatcgcgg atcagcatgc cgcggtgaat     1380
acgttcccgg gccttgtaca caccgcccgt cacaccacga gagtttgcaa cacccgaagt     1440
cggtgaggta acctttatgg agccagccgc cgaaggtggg gcagatgatt ggggtgaagt     1500
cgtaacaagg taaccaaatc actagt                                          1526
```

<210> 10

<211> 1488

<212> DNA

<213> *Ochrobactrum sp*

<400> 10

```
catatggtgc tgctggagcg ctgaagcgac tagtgattgg ttaccttgtt acgacttcac       60
cccagtcgct gaccctaccg tggtcacctg cctccttacg gttagcacag tgccttcggg      120
cagaaccaac tcccatggtg tgacgggcgg tgtgtacaag gcccgggaac gtattcaccg      180
cggcatgctg atccgcgatt actagcgatt ccaacttcat gcactcgagt tgcagagtgc      240
aatccgaact gagatggctt ttggagatta gcttgcgctc gcacgcttgc tgcccactgt      300
caccaccatt gtagcacgtg tgtagcccag cccgtaaggg ccatgaggac ttgacgtcat      360 ccccacccctc ctccagctta tcactggcag tccctttaga gtgcccaacc gaatgatggc    420
aactaaaggc gagggttgcg ctcgttgcgg gacttaaccc aacatctcac gacacgagct      480
gacgacagcc atgcagcacc tgtatccggt ccagccgaac tgaaagacac atctctgtgt      540
ccgcgaccgg tatgtcaagg gctggtaagg ttctgcgcgt tgcttcgaat taaaccacat      600
gctccaccgc ttgtgcgggc ccccgtcaat tcctttgagt tttaatctcg cgaccgtact      660
ccccaggcgg aatgttttaat gcgttagctg cgccaccgaa gtgtaaacac cccgacggct    720
aacattcatc gtttacggcg tggactacca gggtatctaa tcctgtttgc tccccacgct     780
ttcgcacctc agcgtcagta atggaccagt gagccgcctt cgccactggt gttcctccga     840
atatctacga atttcacctc tacactcgga attccactca cctcttccat actcaagact     900
```

```
                                    -continued
ttccagtatc aaaggcagtt ccagagttga gctctgggat ttcacccctg acttaaaagt      960
ccgcctacgt gcgctttacg cccagtaaat ccgaacaacg ctagccccct tcgtattacc     1020
gcggctgctg gcacgaagtt agccggggct tcttctccgg ttaccgtcat tatcttcacc     1080
ggtgaaagag ctttacaatc ctaagacctt catcactcac gcggcatggc tggatcaggc     1140
ttgcgcccat tgtccaatat tccccactgc tgcctcccgt aggagtctgg gccgtgtctc     1200
agtcccagtg tggctgatca tcctctcaga ccagctatgg atcgtcgcct tggtaggcct     1260
ttaccccacc aactagctaa tccaacatgg gctcatcact ctccgataaa tctttcccca     1320
aaagggcgta tacggtatta gcacaagttt ccctgagtta ttccgtagag aatggtagat     1380
tcccatgcat tactcacccg tctgccactg cctccgaaga gaccgttcga cttgcatgtg     1440
ttaagcctgc cgccagcgtt cgttctgagc caggatcaaa ctctaatc                  1488

<210> 11

<211> 1499

<212> DNA

<213> Providencia vermicola

<400> 11
agagtttgat catggctcag attgaacgct ggcggcaggc ctaacacatg caagtcgagc       60
ggtaacaggg gaagcttgct tcccgctgac gagcggcgga cgggtgagta atgtatgggg     120
atctgcccga tagaggggga taaccactgg aaacggtggc taataccgca taatctctca     180
ggagcaaagc aggggaactt cggtccttgc gctatcggat gaacccatat gggattagct     240
agtaggtgag gtaatggctc acctaggcga cgatccctag ctggtctgag aggatgatca     300
gccacactgg gactgagaca cggcccagac tcctacggga ggcagcagtg gggaatattg     360
cacaatgggc gcaagcctga tgcagccatg ccgcgtgtat gaagaaggcc ctagggttgt     420
aaagtacttt cagtcgggag gaaggcgttg atgctaatat catcaacgat tgacgttacc     480
gacagaagaa gcaccggcta actccgtgcc agcagccgcg gtaatacgga gggtgcaagc     540
gttaatcgga attactgggc gtaaagcgca cgcaggcggt tgattaagtt agatgtgaaa     600
tccccgggct taacctggga atggcatcta agactggtca gctagagtct tgtagagggg     660
ggtagaattc catgtgtagc ggtgaaatgc gtagagatgt ggaggaatac cggtggcgaa     720
ggcggccccc tggacaaaga ctgacgctca ggtgcgaaag cgtggggagc aaacaggatt     780
agataccctg gtagtccacg ctgtaaacga tgtcgatttg aaggttgttc ccttgaggag     840
tggctttcgg agctaacgcg ttaaatcgac cgcctgggga gtacggccgc aaggttaaaa     900
ctcaaatgaa ttgacggggg cccgcacaag cggtggagca tgtggtttaa ttcgatgcaa     960
cgcgaagaac ctacctactc ttgacatcca gagaacttag cagagatgct tggtgcctt    1020 cgggaactct gagacaggtg ttgcatggct gtcgtcagct cgtgtcgtga tgttgggt     1080 taagtcccgc aacgagcgca acccttgtca ttagttgcca gcattcagtt gggcactcta     1140
atgagactgc cggtgacaaa ccggaggaag gtgggatga cgtcaagtcc tcatggccct     1200
tatgggtagg gcttcacacg tcatacaatg gtcgggacag agggttgcca aaccgcgagg     1260
tggagccaat ctcagaaacc cgatcgtagt ccggattgca ggctgcaact cgcctgcatg     1320
aagtcggaat cgctagtaat cgcggatcag catgtcgcgg tgaatacgtt cccgggtctt     1380
gtacacaccg cccgtcacac catgggagtg gttttacca gaagtagtta gcctaaccgc     1440
aaggggggcg attaccacgg taggattcat gactggggtg aagtcgtaac aaggtaacc     1499

<210> 12
```

<211> 1545

<212> DNA

<213> Bacillus aerius

<400> 12

```
gattgtttga tcctggctca ggacgaacgc tggcggcgtg cctaatacat gcaagtcgag      60
cggacagatg ggagcttgct ccctgatgtc agcggcggac gggtgagtaa cacgtgggta     120
acctgcctgt aagactggga taactccggg aaaccggggc taataccaga tgcttgattg     180
aaccgcatgg ttcaattata aaaggtggct tttagctacc acttacagat ggacccgcgg     240
cgcattagct agttggtgag gtaacggctc accaaggcaa cgatgcgtag ccgacctgag     300
agggtgatcg ccacactgg gactgagaca cggcccagac tcctacggga ggcagcagta     360
gggaatcttc cgcaatggac gaaagtctga cggagcaacg ccgcgtgagt gatgaaggtt     420
ttcggatcgt aaaactctgt tgttagggaa gaacaagtac cgttcgaata gggcggtacc     480
ttgacggtac ctaaccagaa agccacggct aactacgtgc cagcagccgc ggtaatacgt     540
aggtggcaag cgttgtccgg aattattggg cgtaaagcgc gcgcaggcgg tttcttaagt     600
ctgatgtgaa agcccccggc tcaaccgggg agggtcattg gaaactgggg aacttgagtg     660
cagaagagga gagtggaatt ccacgtgtag cggtgaaatg cgtagagatg tgggaggaac     720
accagtggcg aaggcgactc tctggtctgt aactgacgct gaggcggcga aagcgtgggg     780
agcgaacagg attagatacc ctggtagtcc ccccgtaaa cgatgagtgc taagtgttag     840
agggtttccc cccttttagtg ctgcagcaaa cgcattaagc actccgcctg gggagtacgg     900
gtcgcaagac tgaaactcaa aggaattgac ggggcccgc acaaccggtg gagcatgtgg     960
tttaattcga agcaacgcga agaaccttac caggtcttga catcctctgc caaccctag   1020
agatagggct tcccttcgg gggcagagtg acaggtggtg catggttgtc cgtcagctcg   1080
tgtcgtgaga tgttgggtta agtcccgcac cgagcgcaac ccttgatctt agttgccagc   1140
attcagttgg gcactctaag gtgcctcccg gtgacaaacc ggaggaaggt ggggatgacg   1200
tcaaatcatc atgcccctta tgacctgggc tacacacgtg ctccaatggg cagaacaaag   1260
ggcagcgaag ccgcgaggct aagccaatcc cacaaatctg ttctcagttc ggatcgcagt   1320
ctgcaactcg actgcgtgaa gctggaatcg ctagtaatcg cggatcagca tgccgcggcg   1380
aatacgttcc cgggccttgt acacaccgcc cgtcacacca cgagagtttg taacacccga   1440
agtcggtgag gtaaccttt ggagccagcc gccgaaggtg gacagatga ttggggtgaa    1500
gtcgtaacaa ggtaaccaag tagagtttga tcctgaatca ctagt                  1545
```

<210> 13

<211> 1529

<212> DNA

<213> Bacillus subtilis

<400> 13

```
gattagagtt tgatcatggc tcaggacgaa cgctggcggc gtgcctaata catgcaagtc      60
gagcggacag atgggagctt gctccctgat gtcagcggcg gacgggtgag taacacgtgg     120
gtaacctgcc tgtaagactg ggataactcc gggaaaccgg ggctaatacc aggtgcttga     180
ttgaaccgca tggttcaatt ataaaaggtg gcttttagct accacttaca gatggacccg     240
cggcgcatta gctagttggt gaggtaacgg ctcaccaagg caacgatgcg tagccgacct     300
```

```
                                            -continued
gagagggtga tcggccacac tgggactgag acacggccca gactcctacg ggaggcagca        360
gtagggaatc ttccgcaatg gacgaaagtc tgacggagca acgccgcgtg agtgatgaag        420
gttttcggat cgtaaaactc tgttgttagg gaagaacaag taccgttcga atagggcggt        480
accttgacgg tacctaacca gaaagccacg gctaactacg tgccagcagc cgcggtaata        540
cgtaggtggc aagcgttgtc cggaattatt gggcgtaaag cgcgcgcagg cggtttctta        600
agtctgatgt gaaagccccc ggctcaaccg ggagggtca ttggaaactg ggaacttga          660 gtgcagaaga ggagagtggg aattccacgt gtagcggttg aaatgcgtag agatgtggag        720
gaacaccagt ggcgaaggcg actctctggt ctgtaactga cgctgaggcg cgaaagcgtg        780
gggagcgaac aggattagat accctggta gtccacgccg taaacgatga gtgctaagtg        840
ttagagggtt tccgccctt tagtgctgca gcaaacgcat taagcactcc gcctggggag         900
tacggtcgca agactgaaac tcaaaggaat tgacggggc ccgcacaagc ggtggagcat         960
gtggtttaat tcgaagcaac gcgaagaacc ttaccaggtc ttgacatcct ctgacaaccc       1020
tagagatagg gcttccccttt cggggcaga gtgacaggtg gtgcatggtt gtcgtcagct       1080
cgtgtcgtga tgttgggt taagtcccgc aacgagcgca accttgatc ttagttgcca         1140 gcattcagtt gggcactcta aggtgactgc cggtgacaaa ccggaggaag gtggggatga       1200
cgtcaaatca tcatgcccct tatgacctgg gctacacacg tgctacaatg gcagaacaa        1260 agggcagcga agccgcgagg ctaagccaat cccacaaatc tgttctcagt tcggatcgca       1320
gtctgcaact cgactgcgtg aagctggaat cgctagtaat cgcggatcag catgccgcgg       1380
tgaatacgtt cccgggcctt gtacacaccg cccgtcacac cacgagagtt tgtaacaccc       1440
gaagtcggtg aggtaaccct ttggagccag ccgccgaagg tgggacagat gattggggtg       1500
aagtcgtaac aaggtaacca atcactagt                                         1529

<210> 14

<211> 1526

<212> DNA

<213> Bacillus pumilus

<400> 14
gattagagtt tgatcctggc tcaggacgaa cgctggcggc gtgcctaata catgcaagtc         60
gagcggacag aagggagctt gctcccggat gttagcggcg gacgggtgag taacacgtgg        120
gtaacctgcc tgtaagactg ggataactcc gggaaaccgg agctaatacc ggatagttcc        180
ttgaaccgca tggttcaagg atgaaagacg gtttcggctg tcacttacag atggacccgc        240
ggcgcattag ctagttggtg gggtaatggc tcaccaaggc gacgatgcgt agccgacctg        300
agagggtgat cggccacact gggactgaga cacggcccag actcctacgg gaggcagcag       360
tagggaatct tccgcaatgg acgaaagtct gacggagcaa cgccgcgtga gtgatgaagg       420
ttttcggatc gtaaagctct gttgttaggg aagaacaagt gcgagagtaa ctgctcgcac       480
cttgacggta cctaaccaga aagccacggc taactacgtg ccagcagccg cggtaatacg       540
taggtggcaa gcgttgtccg gaattattgg gcgtaaaggg ctcgcaggcg gtttcttaag       600
tctgatgtga aagccccggg ctcaaccggg agggtcatt ggaaactggg aaacttgagt        660
gcagaagagg agagtggaat tccacgtgta gcggtgaaat gcgtagagat gtggaggaac       720
accagtggcg aaggcgactc tctggtctgt aactgacgct gaggagcgaa agcgtgggga       780
gcgaacagga ttagataccc tggtagtcca cgccgtaaac gatgagtgct aagtgttagg       840
gggtttccgc cccttagtgc tgcagctaac gcattaagca ctccgcctgg ggagtacggt       900
```

-continued

```
cgcaagactg aaactcaaag gaattgacgg gggcccgcac aagcggtgga gcatgtggtt      960
taattcgaag caacgcgaag aaccttacca ggtcttgaca tcgtctgata accctagaga     1020
tagggctttc ccttcgggga cagagtgaca ggtggtgcat ggtcagtcgt cagctcgtgt     1080
cgtgagatgt tgggttaagt cccgcaacgg gcgcaaccct tgatcttagt tgccagcatt     1140
tagttgggca ctcttaaggt gactgccggt gacaaaccgg aggaaggtgg ggatgacgtc     1200
aaatcatcat gccccttatg acctgggcta cacacgtgct acaatggaca gaacaaaggg     1260
ctgcgagacc gcaaggttta gccaatccca taaatctgtt ctcagttcgg atcgcagtct     1320
gcaactcgac tgcgtgaagc tggaatcgct agtaatcgcg gatcagcatg ccgcggtgaa     1380
tacgttcccg ggccttgtac acaccgcccg tcacaccacg ggagtttgca cacccgaag      1440
tcggtgaggt aacctttatg gagccagccg ccgaaggtgg ggcagatgat tggggtgaag     1500
tcgtaacaag gtaaccaatc actagt                                          1526
```

<210> 15

<211> 1526

<212> DNA

<213> *Bacillus sp*

<400> 15

```
gattagagtt tgatcatggc tcaggacgaa cgctggcggc gtgcctaata catgcaagtc       60
gagcggacag aagggagctt gctcccggat gttagcggcg gacgggtgag taacacgtgg      120
gtaacctgcc tgtgagactg ggataactcc gggaaaccgg agctaatacc ggatagttcc      180
ttgaaccgca tggttcaagg atgaaagacg gtttcggctg tcacttacag atggacccgc      240
ggcgcattag ctagttggtg gggtaatggc tcaccaaggc gacgatgcgt agccgacctg      300
agagggtgat cggccacact gggactgaga cacggcccag actcctacgg gaggcagcag      360
tagggaatct tccgcaatgg acgaaagtct gacggagcaa cgccgcgtga gtgatgaagg      420
ttttcggatc gtaaagctct gttgttgggg aagaacaagt gcgagagtaa ctgctcgcac      480
cttgacggta cctaaccaga aagccacggc taactacgtg ccagcagccg cggtaatacg      540
taggtggcaa gcgttgtccg gaattattgg gcgtaaaggg ctcgcaggcg gtttcttaag      600
tctgatgtga aagccccccgg ctcaaccggg gagggtcatt ggaaactggg aaacttgagt      660
gcagaagagg agagtggaat tccacgtgta gcggtgaaat gcgtagagat gtggaggaac      720
accagtggcg aaggcgactc tctggtctgt aactgacgct gaggagcgaa agcgtgggga      780
gcgaacagga ttagataccc tggtagtcca cgccgtaaac gatgagtgct aagtgttagg      840
gggtttccgc cccttagtgc tgcagctaac gcattaagoa ctccgcctgg ggagtacggt      900
cgcaagactg aaactcaaag gaattgacgg gggcccgcac aagcggtgga gcatgtggtt      960
taattcgaag caacgcgaag aaccttacca ggtcttgaca tcctctgata accctagaga     1020
tagggctttc ccttcgggga cagagtgaca ggtggtgcat ggttgtcgtc agctcgtgtc     1080
gtgagatgtt gggttaagtc ccgcaacgag cgcagggggg ggggcttag tagccagcat     1140
ttagttgggc actctaaggt gactgccggt gacaaaccgg aggaaggtgg ggatgacgtc     1200
aaatcatcat gccccttatg acctgggcca cacacgtgct acaatggaca gaacaaaggg     1260
ctgcgagacc gcaaggttta gccaatccca taaatctgtt ctcagttcgg atcgcagtct     1320
gcaactcgac tgcgtgaagc tggaatcgct agtaatcgcg gatcagcatg ccgcggtgaa     1380
tacgttcccg ggccttgtgc acaccgcccg tcacaccacg agagtttgca cacccgaag      1440
```

-continued

```
tcggtgaggt aaccattatg gagccagccg ccgaaggtgg ggcagatgat tggggtgaag        1500
tcgtaacaag gtaaccaatc actagt                                            1526
```

<210> 16

<211> 1524

<212> DNA

<213> Bacillus licheniformis

<400> 16

```
actagtgatt agagtttgat cctggctcag gacgaacgct ggcggcgtgc ctaatacatg          60
caagtcgagc ggacagatgg gagcttgctc cctgatgtta gcggcggacg ggtgagtaac         120
acgtgggtaa cctgcctgta agactgggat aactccggga aaccggggct aataccggat         180
gcttgattga accgcatggt tcaattataa aaggtggctt cggctaccac ttacagatgg         240
acccgcggcg cattagctag ttggtgaggt aacggctcac caaggcaacg atgcgtagcc         300
gacctgagag ggtgatcggc cacactggga ctgagacacg gcccagactc ctacgggagg         360
cagcagtagg gaatcttccg caatggacga aagtctgacg gagcaacgcc gcgtgagtga         420
tgaaggtttt cggatcgtaa aactctgttg ttagggaaga acaagtaccg ttcgaatagg         480
gcggtacctt gacggtacct aaccagaaag ccacggctaa ctacgtgcca gcagccgcgg         540
taatacgtag gtggcaagcg ttgtccggaa ttattgggcg taaagcgcgc gcaggcggtt         600
tcttaagtct gatgtgaaag cccccggctc aaccggggag ggtcattgga aactggggaa         660
cttgagtgca gaagaggaga gtggaattcc acgtgtagcg gtgaaatgcg tagagatgtg         720
gaggaacacc agtggcgaag gcgactctct ggtctgtaac tgacgctgag gcgcgaaggc         780
gtggggagcg aacaggatta gataccctgg tagtccacgc cgtaaacgat gagtgctaag         840
tgttagaggg tttccgccct ttagtgctgc agcaaacgca ttaagcactc cgcctgggga         900
gtacggtcgc aagactgaaa ctcaaaggaa ttgacggggg cccgcacaag cggtggagca         960
tgtggtttaa ttcgaagcaa cgcgaagaac cttaccaggt cttgacatcc tctgacaacc        1020
ctagagatag gcttcccct tcgggggcag agtgacaggt ggtgcatggt tgtcgtcagc        1080
tcgtgtcgtg agatgttggg ttaagtcccg caacgagcgc aacccttgat cttagttgcc        1140
agcattcagt tgggcactct aaggtgactg ccggtgacaa accggaggaa ggtggggatg        1200
acgtcaaatc atcatgcccc ttatgacctg ggctacacac gtgctacaat gggcagaaca        1260
aagggcagcg aagccgcgag gctaagccaa tcccacaaat ctgttctcag ttcggatcgc        1320
agtctgcaac tcgactgcgt gaagctggaa tcgctagtaa tcgcggatca gcatgccgcg        1380
gtgaatacgt tcccgggcct tgtacacacc gcccgtcaca ccacgagagt ttgtaacacc        1440
cgaagtcggt gaggtaacct tttggagcca gccgccgaag gtgggacaga tgattggggt        1500
gaagtcgtaa caaggtaacc aatc                                              1524
```

The invention is further described by the following numbered paragraphs:

1. A consortium of microorganisms capable of hydrolyzing cellulose, preferably lignocellulosic biomass, characterized in that it comprises the following mixtures of bacterial strains: *Bacillus* sp. KP7, KP20 and *Ochrobactrum* sp. KP8 (the mixture deposited in PCM under the no. B/00064), *Providencia* sp. KP14; *Bacillus* sp. KP6 and KP16 (the mixture deposited in PCM under the no. B/00065), *Bacillus* sp. KP4, KP5, KP17 and KP22 (the mixture deposited in PCM under the no. B/00066), *Providencia* sp. KP10; *Bacillus* sp. KP1 and KP19 (the mixture deposited in PCM under the no. B/00067), *Ochrobactrum* sp. K213; *Bacillus* sp. KP9 and KP12 (the mixture deposited in PCM under the no. B/00068).

2. The consortium of microorganisms according to paragraph 1, characterized in that the individual strains in each mixture are mixed in equal proportions.

3. The consortium of microorganisms according to paragraph 2, characterized in that all the mixtures are mixed in an equal quantitative ratio.

4. A preparation for hydrolysis of cellulose, preferably lignocellulosic biomass and/or increasing the efficiency of biogas production in methane fermentation process, and/or revival and/or propagation of methanogenic consortia and/or methanogenic microorganisms themselves, characterized in that it comprises the consortium of microorganisms according to any of the paragraphs 1 to 3, wherein, preferably, the preparation also comprises supplementary and/or auxiliary substances.

5. Use of the consortium of microorganisms according to paragraphs 1-3 and/or the preparation according to paragraph 4 for catalyzing hydrolysis of cellulose, preferably lignocellulosic biomass.

6. The use according to paragraph 5, characterized in that the consortium of microorganisms and/or the preparation are used directly in digesters.

7. The use, according to paragraph 5 or 6, characterized in that it leads to an increased efficiency of biogas production in methane fermentation process.

8. A supplement preparation for supplementing methane fermentation, characterized in that it comprises organic and inorganic substances from the degradation of biomass, produced with the use of the consortium of microorganisms according to any of the paragraphs 1-3 and/or the preparation according to paragraph 4.

9, The supplement preparation according to paragraph 8, characterized in that the organic and inorganic substances from the degradation of biomass are contained in the supernatant obtained after centrifugation of cultures of bacterial strains included in the consortium of microorganisms according to any of the paragraphs 1-3 and/or the preparation according to paragraph 4.

10. The supplement preparation according to paragraph 8 or 9, characterized in that it is added to the medium for methanogenic consortia and/or methanogenic microorganisms themselves at a ratio 1:20 of the medium.

11. A combination preparation for catalyzing hydrolysis of cellulose, preferably lignocellulosic biomass and/or increasing the efficiency of biogas production in methane fermentation process and/or for revival and/or propagation of methanogenic consortia, and/or methanogenic microorganisms themselves, characterized in that it comprises a combination of: a) the consortium of microorganisms capable of hydrolyzing cellulose, according to any of the paragraphs 1-3 and/or the preparation for catalyzing the hydrolysis of cellulose according to paragraph 4, and b) the supplement preparation for supplementation of methane fermentation according to paragraphs 8-10.

12. Use of the consortium of microorganisms according to any of the paragraphs 1-3 and/or the preparation according to paragraph 4 and/or the supplement preparation according to paragraphs 8-10 and/or the combination preparation according to paragraph 11 for revival and/or propagation of methanogenic consortia and/or methanogenic microorganisms themselves.

13. A method of catalyzing hydrolysis of cellulose, preferably lignocellulosic biomass, characterized in that it comprises use of the consortium of microorganisms according to paragraphs 1-3 and/or the preparation according to paragraph 4 and/or the supplement preparation according to paragraph 11.

14. The method according to paragraph 13, characterized in that it leads to an increased efficiency of biogas production in methane fermentation process.

15. The method according to paragraph 13 or 14, characterized in that the consortium of microorganisms and/or the preparation are used directly in digesters.

16. The method according to any of the paragraphs 13-15, characterized in that hydrolysis is carried out under anaerobic conditions at 30° C.

17. The method according to any of the paragraphs 13-16 characterized in that the hydrolysis is carried out at pH 7.

18. The method according to any of the paragraphs 13-17, characterized in that the consortium of microorganisms and/or the preparation are used together with the methanogenic consortium.

19. The method of revival and/or propagation of methanogenic consortia, and/or methanogenic microorganisms themselves, characterized in that it comprises use of the consortium of microorganisms according to paragraphs 1-3 and/or the preparation according to paragraph 4 and/or the supplement preparation according to paragraphs 8-10 and/or the combination preparation according to paragraph 11.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

SEQUENCE LISTING

```
<160> NUMBER OF SEQ ID NOS: 16

<210> SEQ ID NO 1
<211> LENGTH: 1525
<212> TYPE: DNA
<213> ORGANISM: Bacillus licheniformis

<400> SEQUENCE: 1
gattagagtt tgatcctggc tcaggacgaa cgctggcggc gtgcctaata catgcaagtc      60
gagcggaccg acgggagctt gctcccttag gtcagcggcg gacgggtgag taacacgtgg     120
gtaacctgcc tgtaagactg ggataactcc gggaaaccgg ggctaatacc ggatgcttga    180
ttgaaccgca tggttcaatt ataaaaggtg gcttttagct accacttaca gatggacccg    240
cggcgcatta gctagttggt gaggtaacgg ctcaccaagg caacgatgcg tagccgacct    300
gagagggtga tcggccacac tgggactgag acacggccca gactcctacg ggaggcagca    360
gtagggaatc ttccgcaatg gacgaaagtc tgacggagca acgccgcgtg agtgatgaag    420
gttttcggat cgtaaaactc tgttgttagg gaagaacaag taccgttcga ataggcggt     480
```

-continued

```
accttgacgg tacctaacca gaaagccacg gctaactacg tgccagcagc cgcggtaata        540
cgtaggtggc aagcgttgtc cggaattatt gggcgtaaag cgcgcgcagg cggtttctta        600
agtctgatgt gaaagccccc ggctcaaccg ggagggtca ttggaaactg ggaacttga          660 gtgcagaaga ggagagtgga attccacgtg tagcggtgaa atgcgtagag atgtggagga        720
acaccagtgg cgaagcgact ctctggtctg taactgacgc tgaggcgcga aagcgtgggg        780
agcgaacagg attagatacc ctggtagtcc acgccgtaaa cgatgagtgc taagtgttag        840
agggtttccg ccctttagtg ctgcagcaaa cgcattaagc actccgcctg ggagtacgg         900 tcgcaagact gaaactcaaa ggaattgacg ggggcccgca caagcggtgg agcatgtggc        960
ttaattcgaa gcaacgcgaa gaaccttacc aggtcttgac atcctctgac aaccctagag       1020
atagggcttc ccttcgggg gcagagtgac aggtggtgca tggttgtcgt cagctcgtgt        1080
cgtgagatgt tgggttaagt cccgcaacga gcgcaaccct tgatcttagt tgccagcatt      1140
cagttgggca ctctaaggtg actgccggtg acaaaccgga ggaaggtggg gatggcgtca      1200
aatcatcatg cccttatga cctgggctac acacgtgcta caatgggcag aacaaagggc       1260
agcgaagccg cgaggctaag ccaatcccac aaatctgttc tcagttcgga tcgcagtctg      1320
caactcgact gcgtgaagct ggaatcgcta gtaatcgcgg atcagcatgc cgcggtgaat       1380
acgttcccgg gccttgtaca caccgcccgt cacaccacga gagtttgtaa cacccgaagt      1440
cggtgaggta accttttagg agccagccgc cgaaggtggg acagatgatt ggggtgaagt       1500
cgtaacaagg taaccaatca ctagt                                             1525
```

<210> SEQ ID NO 2
<211> LENGTH: 1635
<212> TYPE: DNA
<213> ORGANISM: Bacillus pumilus

<400> SEQUENCE: 2

```
gcgtgtcaac ttcctattgg gggcggagtt gggacgacgt cgcatgctcc cggccggatt         60
agagtttgat cctggctcag gacgaacgct ggcggcgtgc ctaatacatg caagtcgagc        120
gaacagaagg gagcttgctc ccggatgtta gcggcggacg ggtgagtaac acgtgggtaa        180
cctgcctgta agactgggat aactccggga accggagct aataccggat agttccttga         240
accgcatggt tccaaggatga aagacggttt cggctgtcac ttacagatgg acccgcggcg       300
cattagctag ttggtggggt aatggctcac caaggcgacg atgcgtagcc gacctgagag        360
ggtgatcggc cacactgggg ctgagacacg gcccagactc ctacgggagg cagcagtagg       420
gaatcttccg caatggacga aagtctgacg gagcaacgcc gcgtgagtga tgattgtttt       480
cggatcccaa agctctgttg ttagggaaga acaagaggga gaggagctgc tcgcaccttg      540
acggtacgta accagaaagc cacggctaac tacgtgccag ctgccgcggt aatacgtagg       600
tggcaagcgt tgtccgggat tattgggcgt aaagggctcg caggcggttt cttaagtctg      660
atgtgaaagc ccccggctca accggggagg gtcattggag actgggaaac ttgagtgcag      720
aagaggagag tggaattcca cgtgtagcgg tgaaatgctt agagatgtgg aggaacacca       780
gtggcgaatg cgactctctg gtctgtaact gacgctgagg agcgaaagcg tggggagcga        840
caggattaga taccctggta gtccacgccg taaacgatga gtgctaagtg ttagggggt        900 ttccgcccct tagtgctgca gctaacgcat taagcactcc gcctgggag tacgtcgca        960 agactgaaac tcaaaggaat tgacggggc ccgcacaagc ggtggagcat gtggtttaat       1020
```

```
tcgaagcaac gcgaagaacc ttaccaggtc ttgacatcct ctgacaaccc tagagatagg    1080
gctttccctt cggggacaga gtgacaggtg gtgcatgcca gtcgtcagct cgtgtcgcga    1140
catgttgggt taagtcccgc aacgagcgca gcccttgatc ttagttgcca gcatttagtt    1200
gggcactcta aggtgactgc cggtgacaaa ccggaggaag gtggggatga cgtcaaatca    1260
tcatgcccct tatgacctgg gctacacacg tgctacaatg gacagaacaa agggttgcga    1320
gaccgcaagg tttagccaat cccataaatc tgttctcagt tcggatcgca gtctgcaact    1380
cgactgcgtg aagctggaat cgctagtaat cgcggatcag catgccgcgg tgaatacgtt    1440
cccgggcctt gtacacaccg cccgtcacac cacgagagtt gtaaacaccc gaagtcggtg    1500
aggtaacctt tatggagcca gccgccgaag gtgggacaga tgattggggt gaagtcgtaa    1560
caaggtaacc aatcactagt cgcgttggat gcatagcttg agtattctaa tacggtcacc    1620
aaaattacct tgtta                                                    1635

<210> SEQ ID NO 3
<211> LENGTH: 1620
<212> TYPE: DNA
<213> ORGANISM: Bacillus pumilus

<400> SEQUENCE: 3 ctataggcg attgggcccg acgtcgcatg ctcccggccg gattagagtt tgatcctggc      60
tcaggacgaa cgctggcggc gtgcctaata catgcaagtc gagcgaacag aagggagctt     120
gctcccggat gttagcggcg gacgggtgag taacacgtgg gtaacctgcc tgtaagactg     180
ggataactcc gggaaaccgg agctaatacc ggatagttcc ttgaaccgca tggttcaagg     240
gtgaaagacg gtttcggctg tcacttacag atggacccgc ggcgcattag ctagttggtg     300
gggtaatggc tcaccaaggc gacgatgcgt agccgacctg agagggtgat cggccacact     360
gggactgaga cacggcccag actcctacgg gaggcagcag tagggaatct tccgcaatgg     420
acgaaagtct gacggagcaa cgccgcgtga gtgatgaagg ttttcggatc gtaaagctct     480
gttgttaggg aagaacaagt gcgagagtaa ctgctcgcac cttgacgtgg cctaaccaga     540
aagccacggc tagctacgtg ccagcagccg cggtaatacg taggtggcaa gcgttgtccg     600
gaattattgg gcgtaaaggg ctcgcaggcg gtttcttaag gtctgatgtg aaagccccg      660 gctcaaccgg ggagggtcat tggaaactgg gaaacttgag tgcagaagag gagagtggaa     720
ttccacgtgt agcggtgaaa tgcgtagaga tgtggaggaa caccagtggc gaaggcgact     780
ctctggtctg taactgacgc tgaggagcga aagcgtgggg agcgaacagg attagatacc     840
ctggtagtca cgccgtaaac gatgagtgct aagtgtttgg gggtttccgc cccttagtg     900 ctgcagctaa cgcattaagc actccgcctg gggagtacgg tcgcaagact gaaactcaaa     960
ggaattgacg ggcccgca caagcggtgg agcatgtggt ttaattcgaa gcaacgcgaa      1020
gatccttgtc aggtcttgac atcctctgac aaccctagag acaggctttt ccttcgggg     1080 acagagtgac aggtggtgcc atggttgtcg tcagctcgtg tcgtgagatg ttgggttaag    1140
tcccgcaacg agcgcaaccc ttgatgttag ttgccagcat ttagttgggc actctaaggt    1200
gactgccggt gacaaaccgg aggaaggtgg ggatgacgtc aaatcatcat gccccttatg    1260
acctgggcta cacacgtgct acaatggaca gaacaaaggg ctgcgagacc gcaaggttta    1320
gccaatccca taaatctgtt ctcagttcgg atcgcagtct gcaactcgac tgcgtgaagc    1380
tggaatcgct agtaatcgcg gatcagtatg ccgcggtgaa tacgttcccg ggccttgtac    1440
acaccgcccg tcacaccacg agagtttgta acacccgaag tcggtgaggt aacctttatg    1500
```

| gagccagccg ccgaaggtgg gacagatgat tggggtgaag tcgtaacaag gtaaccaatc | 1560 |
| actagtaacg cgttggatgc atagcttgag tattctatag ttcacccaaa aaaggcccc | 1620 |

<210> SEQ ID NO 4
<211> LENGTH: 1527
<212> TYPE: DNA
<213> ORGANISM: Bacillus pumilus

<400> SEQUENCE: 4

| gattaccagt ttgatcctgg ctcaggacga acgctggcgg cgtgcctaat acatgcaagt | 60 |
| cgagcggaca aagggagct tgctcccgga tgttagcggc ggacgggtga gtaacacgtg | 120 |
| ggtaacctgc ctgtaagact gggataactc cgggaaaccg gagctaatac cggatagttc | 180 |
| cttgaaccgc atggttcaag gatgaaagac ggtttcggct gtcacttaca gatggacccg | 240 |
| cggcgcatta gctagttggt ggggtaatgg ctcaccaagg cgacgatgcg tagccgacct | 300 |
| gagagggtga tcggccacac tgggactgag acacggccca gactcctacg ggaggcagca | 360 |
| gtagggaatc ttccgcaatg gacgaaagtc tgacggagca acgccgcgtg agtgatgaag | 420 |
| gttttcggat cgtaaagctc tgttgttagg gaagaacaag tgcgagagta actactcgca | 480 |
| ccttgacggt acctaaccag aaagccacgg ctaactacgt gccagcagcc gcggtaatac | 540 |
| gtaggtggca agcgttgtcc ggaattattg ggcgtaaagg ctcgcaggc ggtttcttaa | 600 |
| gtctgatgtg aaagccccg gctcaaccgg ggagggtcat tggaaactgg gaaacttgag | 660 |
| ttgcagaaga ggagagtgga attccacgtg tagcggtgaa atgcgtagag atgtggagga | 720 |
| acaccagtgg cgaaggcgac tctctggtct gtaaactgac gctgaggagc gaaagcgtgg | 780 |
| ggagcgaaca ggattagata ccctggtagt ccacgccgta acgatgagt gctaagtgtt | 840 |
| aggggggtttc cgccccttag tgctgcagct aacgcattaa gcactccgcc tggggagtac | 900 |
| ggtcgcaaga ctgaaactca aaggaattga cggggccccg cacaagcggt ggagcatgtg | 960 |
| gtttaattcg aagcaacgcg aagaaccttac ccaggtcttg acatcctctg acaaccctag | 1020 |
| agatagggct ttcccttcgg ggacagagtg acaggtggtg catggttgtc gtcagctcgt | 1080 |
| gtcgtgagat gttgggttaa gtcccgcaac gagcgcaacc cttgatctta gttgccagca | 1140 |
| tttagttggg cactctaagg tgactgccgg tgacaaaccg gaggaaggtg gggatgacgt | 1200 |
| caaatcatca tgccccttat gacctgggct acacacgtgc tacaatggac agaacaaagg | 1260 |
| gctgcgagac cgcaaggttt agccaatccc ataaatctgt tctcagttcg gatcgcagtc | 1320 |
| tgcaactcga ctgcgtgaag ctggaatcgc tagtaatcgc ggatcagcat gccgcggtga | 1380 |
| atacgttccc gggccttgta cacaccgccc gtcacaccac gagagtttgc aacacccgaa | 1440 |
| gtcggtgagg taacctttat ggagccagcc gccgaaggtg gggcagatga ttggggtgaa | 1500 |
| gtcgtaacaa ggtaaccaat cactagt | 1527 |

<210> SEQ ID NO 5
<211> LENGTH: 1408
<212> TYPE: DNA
<213> ORGANISM: Bacillus altitudinis

<400> SEQUENCE: 5

| aaggtaacca agtagagttt gatcctggct cattaagtcg taacaaggta accaagtaga | 60 |
| gtttgatcct ggcgcaaacc gtcgcaacaa gggacccgtt ccttgaaccg catggttcaa | 120 |
| ggatgaaaga cggtttcggc tgtcacttac agatggaccc gcggcgcatt agctagttgg | 180 |

-continued

```
tgaggtaacg gctcaccaag gcgacgatgc gtagccgacc tgagagggtg atcggccaca      240
ctgggactga gacacggccc acactcctac gggaggcagc agtagggaat cttccgcaat      300
ggacgaaagt ctgacggagc aacgccgcgt gagtgatgaa ggttttcgga tcgtaaagct      360
ctgttgttag gaagaacaa gtgcaagagt aactgcttgc accttgacgg tacctaacca       420
gaaagccacg gctaactacg tgccagcagc cgcggtaata cgtaggtggc aagcgttgtc      480
cggaattatt gggcgtaaag ggctcgcagg cggtttctta agtctgatgt gaaagccccc      540
ggctcaaccg ggagggtca ttggaaactg gaaacttga gtgcagaaga ggagagtgga        600
attccacgtg tagcggtgaa atgcgtagag atgtggagga acaccagtgg cgaaggcgac      660
tctctggtct gtaactgacg ctgaggagcg aaagcgtggg gagcgaacag gattagatac      720
cctggtagtc cacgccgtaa acgatgagtg ctaagtgtta gggggttcc gccccttagt       780 gctgcagcta acgcattaag cactccgcct ggggagtacg gtcgcaagac tgaaactcaa      840
aggaattgac gggggcccgc acaagcggtg gagcatgtgg tttaattcga agcaacgcga      900
agaaccttac caggtcttga catcctctga caacccctaga gatagggctt tcccttcggg     960
gacagagtga caggtggtgc atggttgtcg tcagctcgtg tcgtgagatg ttgggttaag     1020
tcccgcaacg agcgcaaccc ttgatcttag ttgccagcat tcagttgggc actctaaggt    1080
gactgccggt gacaaaccgg aggaaggtgg ggatgacgtc aaatcatcat gccccttatg    1140
acctgggcta cacacgtgct acaatggaca gaacaaaggg ctgcgagacc gcaaggttta    1200
gccaatccca caaatctgtt ctcagtgatc atggctgtgt aagtcgtaac aaggtaacca    1260
agtagagttt gatcctggct cagtaagttg taacaaggta accaagtaga gtttgatcct    1320
ggctcagtaa gtcgtaacaa ggtaaccaag tagagtttga tcctggctca gtaagtcgga    1380
acaaaggaac caacttgggt tgtctgcg                                         1408
```

<210> SEQ ID NO 6
<211> LENGTH: 1459
<212> TYPE: DNA
<213> ORGANISM: Ochrobactrum sp

<400> SEQUENCE: 6

```
gattagagtt tgatcatggc tcagaacgaa cgctggcggc aggcttaaca catgcaagtc       60
gaacggtctc ttcggaggca gtggcagacg ggtgagtaat gcatgggaat ctaccattct      120
ctacggaata actcagggaa acttgtgcta ataccgtata cgcccttttg gggaaagatt      180
tatcggagag tgatgagccc atgttggatt agctagttgg tggggtaaag gcctaccaag     240
gcgacgatcc atagctggtc tgagaggatg atcagccaca ctgggactga gacacggccc     300
agactcctac gggaggcagc agtggggaat attggacaat gggcgcaagc ctgatccagc     360
catgccgcgt gagtgatgaa ggtcttagga ttgtaaagct ctttcaccgg tgaagataat     420
gacggtaacc ggagaagaag ccccggctaa cttcgtgcca gcagccgcgg taatacgaag     480
ggggctagcg ttgttcggat ttactgggcg taaagcgcac gtaggcggac ttttaagtca     540
ggggtgaaat cccagagctc aactctggaa ctgcctttga tactggaagt cttgagtatg     600
gaagaggtga gtggaattcc gagtgtagag gtgaaattcg tagatattcg gaggaacacc     660
agtggcgaag gcggctcact ggtccattac tgacgctgag gtgcgaaagc gtgggagca     720 aacaggatta gataccctgg tagtccacgc cgtaaacgat gaatgttagc cgtcggggtg    780
tttacacttc ggtggcgcag ctaacgcatt aaacattccg cctggggagt acggtcgcaa    840
gattaaaact caaaggaatt gacgggggcc cgcacaagcg gtggagcatg tggtttaatt    900
```

```
cgaagcaacg cgcagaacct taccagccct tgacataccg gtcgcggaca cagagatgtg    960
tctttcagtt cggctggacc ggatacaggt gctgcatggc tgtcgtcagc tcgtgtcgtg   1020
agatgttggg ttaagtcccg caacgagcgc aaccctcgcc tttagttgcc atcatttggt   1080
tgggcactct aaagggactg ccagtgataa gctggaggaa ggtggggatg acgtcaagtc   1140
ctcatggccc ttacgggctg gctacacacg tgctacaat ggtggtgaca gtgggcagca   1200
agcgtgcgag cgcaagctaa tctccaaaag ccatctcagt tcggattgca ctctgcaact   1260
cgagtgcatg aagttggaat cgctagtaat cgcggatcag catgccgcgg tgaatacgtt   1320
cccgggcctt gtacacaccg cccgtcacac catgggagtt ggttctgccc gaaggcactg   1380
tgctaaccgt aaggaggcag gtgaccacgg tagggtcagc gactggggtg aagtcgtaac   1440
aaggtaacca atcactagt                                                1459

<210> SEQ ID NO 7
<211> LENGTH: 1526
<212> TYPE: DNA
<213> ORGANISM: Bacillus sp.

<400> SEQUENCE: 7
gattagagtt tgatcctggc tcaggacgaa cgctggcggc gtgcctaata catgcaagtc     60
gagcggacag aagggagctt gctcccggat gttagcggcg gacgggtgag taacacgtgg    120
gtaacctgcc tgtaagactg ggataactcc gggaaaccgg agctaatacc ggatagttcc    180
ttgaaccgca tggttcaagg atgaaagacg gtttcggctg tcacttacag atggacccgc    240
ggcgcattag ctagttggtg aggtaacggc tcaccaaggc gacgatgcgt agccgacctg    300
agagggtgat cggccacact gggactgaga cacggcccag actcctacgg gaggcagcag    360
tagggaatct tccgcaatgg acgaaagtct gacggagcaa cgccgcgtga gtgatgaagg    420
ttttcggatc gtaaagctct gttgttaggg aagaacaagt gcaagagtaa ctgcttgcac    480
cttgacggta cctaaccaga aagccacggc taactacgtg ccagcagccg cggtaatacg    540
taggtggcaa gcgttgtccg gaattattgg gcgtaaaggg ctcgcaggcg gtttcttaag    600
tctgatgtga aagcccccgg ctcaaccggg gagggtcatt ggaaactggg aaacttgagt    660
gcagaagagg gagagtggaa ttccacgtgt agcggtgaaa tgcgtagaga tgtggaggaa    720
caccagtggc gaaggcgact ctctggtctg taactgacgc tgaggagcga aagcgtgggg    780
agcgaacagg attagatacc ctggtagtcc acgccgtaaa cgatgagtgc taagtgttag    840
ggggtttccc gccccttagt gctgcagcta acgcattaag cactccgcct ggggagtacg    900
gtcgcaagac tgaaactcaa aggaattgac ggggcccgc acaagcggtg aagcatgtgg    960
tttaattcga agcaacgcga agaaccttac caggtcttga catcctctga caaccctaga   1020
gatagggctt tcccttcggg acagagtgac aggtggtgc atggttgtcg tcagctcgtg   1080
tcgtgagatg ttgggttaag tcccgcaacg agcgcaaccc ttgatcttag ttgccagcat   1140
tcagttgggc actctaaggt gactgccggt gacaaaccgg aggaaggtgg ggatgacgtc   1200
aaatcatcat gccccttatg acctgggcta cacacgtgct acaatggaca gaacaaaggg   1260
ttgcgagacc gcaaggttta gccaatccca caaatctgtt ctcagttcgg atcgcagtct   1320
gcaactcgac tgcgtgaagc tggaatcgct agtaatcgcg gatcagcatg ccgcggtgaa   1380
tacgttcccg ggccttgtac acaccgcccg tcacaccacg agagtttgca acacccgaag   1440
tcggtgaggt aacctttatg gagccagccg ccgaaggtgg ggcagatgat tggggtgaag   1500
```

```
tcgtaacaag gtaaccaatc actagt                                          1526
```

<210> SEQ ID NO 8
<211> LENGTH: 1518
<212> TYPE: DNA
<213> ORGANISM: Providencia vermicola

<400> SEQUENCE: 8

```
gattagagtt tgatcatggc tcagattgaa cgctggcggc aggcctaaca catgcaagtc      60
gagcggtaac aggggaagct tgcttcccgc tgacgagcgg cggacgggtg agtaatgtat     120
ggggatctgc ccgatagagg gggataacca ctggaaacgg tggctaatac cgcataatct     180
ctcaggagca aagcagggga acttcggtcc ttgcgctatc ggatgaaccc atatgggatt     240
agctagtagg tgaggtaatg gctcacctgg cgacgatcc ctagctggtc tgagaggatg      300
atcagccaca ctgggactga gacacggccc agactcctac gggaggcagc agtggggaat     360
attgcacaat gggcgcaagc ctgatgcagc catgccgcgt gtatgaagaa ggccctaggg     420
ttgtaaagta ctttcagtcg gaggaaggc gttgatgcta atatcatcaa cgattgacgt      480
tatcgacaga agaagcaccg gctaactccg tgccagcagc cgcggtaata cggagggtgc     540
aagcgttaat cggaattact gggcgtaaag cgcacgcagg cggttgatta agttagatgt     600
gaaatccccg gcttaacct gggaatggca tctaagactg gtcagctaga gtcttgtaga      660
ggggggtaga attccatgtg tagcggtgaa atgcgtagag atgtggagga ttacccggtg     720
ggcgaaggcg gccccctgga caaagactga cgctcaggtg cgaaagcgtg gggagcaaac     780
aggattagat accctggtag tccacgctgt aaacgatgtc gatttgaagg ttgttccctt     840
gaggagtggc ttttcggagc taacgcgtta atcgaccgc ctggggagta cggccgcaag      900
gttaaaactc aaatgaattg acgggggccc gcacaagcgg tggagcatgt ggtttaattc     960
gatgcaacgc gaagaacctt acctactctt gacatccaga gaacttagca gagatgcttt    1020
ggtgccttcg ggaactctga cacaggtgct gcatggctgc cgtcagctcg tgttgtgaaa    1080
tgttgggtta agtcccgcaa cgagcgcaac ccttatcctt gttgccagc gattcggtcg     1140
ggaactcaaa ggagactgcc ggtgataaac cggaggaagg tggggatgac gtcaagtcat    1200
catggccctt acgagtaggg ctacacacgt gctacaatgg cgtatacaaa gagaagcgac    1260
ctcgcgaggg caagcggaac tcataaagta cgtcgtagtc cggattggag tctgcaactc    1320
gactccatga agtcggaatc gctagtaatc gtagatcaga atgctacggt gaatacgttc    1380
ccgggccttg tacaccgc ccgtcacacc atgggagtgg gttgcaaaag aagtaggtag     1440
cttaacctgc gggagggcgc ttaccacttt gtgattcatg actggggtga agtcgtaaca    1500
aggtaaccaa tcactagt                                                  1518
```

<210> SEQ ID NO 9
<211> LENGTH: 1526
<212> TYPE: DNA
<213> ORGANISM: Bacillus sp.

<400> SEQUENCE: 9

```
gattagagtt tgatcatggc tcaggacgaa cgctggcggc gtgcctaata catgcaagtc      60
gagcggacag aagggagctt gctccccggat gttagcggcg gacgggtgag taacacgtgg    120
gtaacctgcc tgtaagactg ggataactcc gggaaaccgg agctaatacc ggaaagttcc    180
ttgaaccgca tggttcaagg atgaaagacg gtttcggctg tcacttacag atggacccgc    240
ggcgcattag ctagttggtg gggtaatggc tcaccaaggc gacgatgcgt agccgacctg    300
```

```
agagggtggt cggccacact gggactgaga cacggcccag actcctacgg gaggcagcag    360
tagggaatct tccgcaatgg acgaaagtct gacggagcaa cgccgcgtga gtgatgaagg    420
ttttcggatc gtaaagctct gttgttaggg aagaacaagt gcgagagtaa ctactcgcac    480
cttgacggta cctaaccaga aagccacggc taactacgtg ccagcagccg cggtaatacg    540
taggtggcaa gcgttgtccg gaattattgg gcgtaaaggg ctcgcaggcg gtttcttaag    600
tctgatgtga aagcccccgg ctcaaccggg gagggtcatt ggaaactggg aaacttgagt    660
gcagaagagg agagtgggat tccacgtgta gcggtgaaat gcgtagagat gtggagggaa    720
caccagtggc gaaggcgact ctctggtctg taactgacgc tgaggagcga aagcgtgggg    780
agcgaacagg attagatacc ctggtagtcc acgccgtaaa cgatgagtgc taagtgttag    840
ggggtttccg ccccttagtg ctgcagctaa cgcattaagc actccgcctg ggagtacggt    900 cgcaagact gaaactcaaa ggaattgacg ggggcccgca caagcggtgg agcatgtggt    960
ttaattcgaa gcaacgcgaa gaaccttacc aggtcttgac atcctctgac aaccctagag   1020
atagggcttt cccttcgggg acagagtgac aggtggtgca tggttgtcgt cagctcgtgt   1080
cgtgagatgt tgggttaagt cccgcaacga gcgcaacccc tgatcttagt tgccagcatt   1140
tagttgggca ctctaaggtg actgccggtg acaaaccgga ggaaggtggg gatgacgtca   1200
aatcatcatg ccccttatga cctgggctac acacgtgcta cagtggacag aacaaagggc   1260
tgcgagaccg caaggtttag ccaatcccat gaatctgttc tcagttcgga tcgcagtctg   1320
caactcgact gcgtgaagct ggaatcgcta gtaatcgcgg atcagcatgc cgcggtgaat   1380
acgttcccgg gccttgtaca caccgcccgt cacaccacga gagtttgcaa cacccgaagt   1440
cggtgaggta acctttatgg agccagccgc cgaaggtggg gcagatgatt ggggtgaagt   1500
cgtaacaagg taaccaaatc actagt                                         1526
```

<210> SEQ ID NO 10
<211> LENGTH: 1488
<212> TYPE: DNA
<213> ORGANISM: Ochrobactrum sp

<400> SEQUENCE: 10

```
catatggtgc tgctggagcg ctgaagcgac tagtgattgg ttaccttgtt acgacttcac     60
cccagtcgct gaccctaccg tggtcacctg cctccttacg gttagcacag tgccttcggg    120
cagaaccaac tcccatggtg tgacgggcgg tgtgtacaag gcccgggaac gtattcaccg    180
cggcatgctg atccgcgatt actagcgatt ccaacttcat gcactcgagt tgcagagtgc    240
aatccgaact gagatggctt ttggagatta gcttgcgctc gcacgcttgc tgcccactgt    300
caccaccatt gtagcacgtg tgtagcccag cccgtaaggg ccatgaggac ttgacgtcat    360 ccccacccctc ctccagctta tcactggcag tccctttaga gtgcccaacc gaatgatggc    420
aactaaaggc gagggttgcg ctcgttgcgg gacttaaccc aacatctcac gacacgagct    480
gacgacagcc atgcagcacc tgtatccggt ccagccgaac tgaaagacac atctctgtgt    540
ccgcgaccgg tatgtcaagg gctggtaagg ttctgcgcgt tgcttcgaat taaaccacat    600
gctccaccgc ttgtgcgggc ccccgtcaat tcctttgagt tttaatctcg gaccgtact    660 ccccaggcgg aatgtttaat gcgttagctg cgccaccgaa gtgtaaacac cccgacggct    720
aacattcatc gtttacggcg tggactacca gggtatctaa tcctgtttgc tccccacgct    780
ttcgcacctc agcgtcagta atggaccagt gagccgcctt cgccactggt gttcctccga    840
```

```
atatctacga atttcacctc tacactcgga attccactca cctcttccat actcaagact    900
ttccagtatc aaaggcagtt ccagagttga gctctgggat ttcacccctg acttaaaagt    960
ccgcctacgt gcgctttacg cccagtaaat ccgaacaacg ctagcccect tcgtattacc   1020
gcggctgctg gcacgaagtt agccggggct tcttctccgg ttaccgtcat tatcttcacc   1080
ggtgaaagag ctttacaatc ctaagacctt catcactcac gcggcatggc tggatcaggc   1140
ttgcgcccat tgtccaatat tccccactgc tgcctcccgt aggagtctgg gccgtgtctc   1200
agtcccagtg tggctgatca tcctctcaga ccagctatgg atcgtcgcct tggtaggcct   1260
ttaccccacc aactagctaa tccaacatgg gctcatcact ctccgataaa tctttcccca   1320
aaagggcgta tacggtatta gcacaagttt ccctgagtta ttccgtagag aatggtagat   1380
tcccatgcat tactcacccg tctgccactg cctccgaaga gaccgttcga cttgcatgtg   1440
ttaagcctgc cgccagcgtt cgttctgagc caggatcaaa ctctaatc                1488
```

<210> SEQ ID NO 11
<211> LENGTH: 1499
<212> TYPE: DNA
<213> ORGANISM: Providencia vermicola

<400> SEQUENCE: 11

```
agagtttgat catggctcag attgaacgct ggcggcaggc ctaacacatg caagtcgagc     60
ggtaacaggg gaagcttgct tcccgctgac gagcggcgga cgggtgagta atgtatgggg    120
atctgcccga tagaggggga taaccactgg aaacggtggc taataccgca taatctctca    180
ggagcaaagc aggggaactt cggtccttgc gctatcggat gaacccatat gggattagct    240
agtaggtgag gtaatggctc acctaggcga cgatccctag ctggtctgag aggatgatca    300
gccacactgg gactgagaca cggcccagac tcctacggga ggcagcagtg gggaatattg    360
cacaatgggc gcaagcctga tgcagccatg ccgcgtgtat gaagaaggcc ctagggttgt    420
aaagtacttt cagtcgggag gaaggcgttg atgctaatat catcaacgat tgacgttacc    480
gacagaagaa gcaccggcta actccgtgcc agcagccgcg gtaatacgga gggtgcaagc    540
gttaatcgga attactgggc gtaaagcgca cgcaggcggt tgattaagtt agatgtgaaa    600
tccccgggct taacctggga atggcatcta agactggtca gctagagtct tgtagagggg    660
ggtagaattc catgtgtagc ggtgaaatgc gtagagatgt ggaggaatac cggtggcgaa    720
ggcggccccc tggacaaaga ctgacgctca ggtgcgaaag cgtggggagc aaacaggatt    780
agataccctg gtagtccacg ctgtaaacga tgtcgatttg aaggttgttc ccttgaggag    840
tggctttcgg agctaacgcg ttaaatcgac cgcctgggga gtacggccgc aaggttaaaa    900
ctcaaatgaa ttgacggggg cccgcacaag cggtggagca tgtggtttaa ttcgatgcaa    960
cgcgaagaac ctacctactc ttgacatcca gagaacttag cagagatgct tggtgccttc   1020
gggaactct gagacaggtg ctgcatggct gtcgtcagct cgtgtcgtga tgttgggt     1080
taagtcccgc aacgagcgca acccttgtca ttagttgcca gcattcagtt gggcactcta   1140
atgagactgc cggtgacaaa ccggaggaag gtggggatga cgtcaagtcc tcatggccct   1200
tatgggtagg gcttcacacg tcatacaatg gtcgggacag agggttgcca aaccgcgagg   1260
tggagccaat ctcagaaacc cgatcgtagt ccggattgca ggctgcaact cgcctgcatg   1320
aagtcggaat cgctagtaat cgcggatcag catgtcgcgg tgaatacgtt cccgggtctt   1380
gtacacaccg cccgtcacac catggagtg ggttttacca gaagtagtta gcctaaccgc    1440
aagggggggcg attaccacgg taggattcat gactgggtg aagtcgtaac aaggtaacc    1499
```

<210> SEQ ID NO 12
<211> LENGTH: 1545
<212> TYPE: DNA
<213> ORGANISM: Bacillus aerius

<400> SEQUENCE: 12

| | | | | | |
|---|---|---|---|---|---|
| gattgtttga | tcctggctca | ggacgaacgc | tggcggcgtg | cctaatacat gcaagtcgag | 60 |
| cggacagatg | ggagcttgct | ccctgatgtc | agcggcggac | gggtgagtaa cacgtgggta | 120 |
| acctgcctgt | aagactggga | taactccggg | aaaccggggc | taataccaga tgcttgattg | 180 |
| aaccgcatgg | ttcaattata | aaaggtggct | tttagctacc | acttacagat ggacccgcgg | 240 |
| cgcattagct | agttggtgag | gtaacggctc | accaaggcaa | cgatgcgtag ccgacctgag | 300 |
| agggtgatcg | gccacactgg | gactgagaca | cggcccagac | tcctacggga ggcagcagta | 360 |
| gggaatcttc | cgcaatggac | gaaagtctga | cggagcaacg | ccgcgtgagt gatgaaggtt | 420 |
| ttcggatcgt | aaaactctgt | tgttagggaa | gaacaagtac | cgttcgaata gggcggtacc | 480 |
| ttgacggtac | ctaaccagaa | agccacggct | aactacgtgc | cagcagccgc ggtaatacgt | 540 |
| aggtggcaag | cgttgtccgg | aattattggg | cgtaaagcgc | gcgcaggcgg tttcttaagt | 600 |
| ctgatgtgaa | agcccccggc | tcaaccgggg | agggtcattg | gaaactgggg aacttgagtg | 660 |
| cagaagagga | gagtggaatt | ccacgtgtag | cggtgaaatg | cgtagagatg tgggaggaac | 720 |
| accagtggcg | aaggcgactc | tctggtctgt | aactgacgct | gaggcggcga aagcgtgggg | 780 |
| agcgaacagg | attagatacc | ctggtagtcc | cccccgtaaa | cgatgagtgc taagtgttag | 840 |
| agggtttccc | ccctttagtg | ctgcagcaaa | cgcattaagc | actccgcctg gggagtacgg | 900 |
| gtcgcaagac | tgaaactcaa | aggaattgac | ggggcccgc | acaaccggtg gagcatgtgg | 960 |
| tttaattcga | agcaacgcga | agaaccttac | caggtcttga | catcctctgc aaccccctag | 1020 |
| agatagggct | tccccttcgg | gggcagagtg | acaggtggtg | catggttgtc gtcagctcg | 1080 |
| tgtcgtgaga | tgttgggtta | agtcccgcac | cgagcgcaac | ccttgatctt agttgccagc | 1140 |
| attcagttgg | gcactctaag | gtgcctcccg | gtgacaaacc | ggaggaaggt ggggatgacg | 1200 |
| tcaaatcatc | atgccccta | tgacctgggc | tacacacgtg | ctccaatggg cagaacaaag | 1260 |
| ggcagcgaag | ccgcgaggct | aagccaatcc | cacaaatctg | ttctcagttc ggatcgcagt | 1320 |
| ctgcaactcg | actgcgtgaa | gctggaatcg | ctagtaatcg | cggatcagca tgccgcggcg | 1380 |
| aatacgttcc | cgggccttgt | acacaccgcc | cgtcacacca | cgagagtttg taacacccga | 1440 |
| agtcggtgag | gtaacctttt | ggagccagcc | gccgaaggtg | gacagatga ttggggtgaa | 1500 |
| gtcgtaacaa | ggtaaccaag | tagagtttga | tcctgaatca | ctagt | 1545 |

<210> SEQ ID NO 13
<211> LENGTH: 1529
<212> TYPE: DNA
<213> ORGANISM: Bacillus subtilis

<400> SEQUENCE: 13

| | | | | | |
|---|---|---|---|---|---|
| gattagagtt | tgatcatggc | tcaggacgaa | cgctggcggc | gtgcctaata catgcaagtc | 60 |
| gagcggacag | atgggagctt | gctccctgat | gtcagcggcg | gacgggtgag taacacgtgg | 120 |
| gtaacctgcc | tgtaagactg | ggataactcc | gggaaaccgg | ggctaatacc aggtgcttga | 180 |
| ttgaaccgca | tggttcaatt | ataaaaggtg | gcttttagct | accacttaca gatgacccg | 240 |
| cggcgcatta | gctagttggt | gaggtaacgg | ctcaccaagg | caacgatgcg tagccgacct | 300 |

```
gagagggtga tcggccacac tgggactgag acacggccca gactcctacg ggaggcagca      360
gtagggaatc ttccgcaatg gacgaaagtc tgacggagca acgccgcgtg agtgatgaag      420
gttttcggat cgtaaaactc tgttgttagg gaagaacaag taccgttcga atagggcggt      480
accttgacgg tacctaacca gaaagccacg gctaactacg tgccagcagc cgcggtaata      540
cgtaggtggc aagcgttgtc cggaattatt gggcgtaaag cgcgcgcagg cggtttctta      600
agtctgatgt gaaagccccc ggctcaaccg ggagggtca ttggaaactg ggaacttga       660
gtgcagaaga ggagagtggg aattccacgt gtagcggttg aaatgcgtag agatgtggag      720
gaacaccagt ggcgaaggcg actctctggt ctgtaactga cgctgaggcg cgaaagcgtg      780
gggagcgaac aggattagat accctggta gtccacgccg taaacgatga gtgctaagtg      840
ttagagggtt tccgccctt tagtgctgca gcaaacgcat taagcactcc gcctggggag      900
tacggtcgca agactgaaac tcaaaggaat tgacggggc cgcacaagc ggtggagcat       960
gtggtttaat tcgaagcaac gcgaagaacc ttaccaggtc ttgacatcct ctgacaaccc     1020
tagagatagg gcttcccctt cggggcaga gtgacaggtg gtgcatggtt gtcgtcagct     1080
cgtgtcgtga tgttgggt taagtcccgc aacgagcgca accttgatc ttagttgcca      1140
gcattcagtt gggcactcta aggtgactgc cggtgacaaa ccgaggaag gtggggatga     1200
cgtcaaatca tcatgcccct tatgacctgg gctacacacg tgctacaatg gcagaacaa     1260
agggcagcga agccgcgagg ctaagccaat cccacaaatc tgttctcagt tcggatcgca     1320
gtctgcaact cgactgcgtg aagctggaat cgctagtaat cgcggatcag catgccgcgg     1380
tgaatacgtt cccgggcctt gtacacaccg cccgtcacac cacgagagtt tgtaacaccc     1440
gaagtcggtg aggtaacctt ttggagccag ccgccgaagg tgggacagat gattggggtg     1500
aagtcgtaac aaggtaacca atcactagt                                       1529

<210> SEQ ID NO 14
<211> LENGTH: 1526
<212> TYPE: DNA
<213> ORGANISM: Bacillus pumilus

<400> SEQUENCE: 14
gattagagtt tgatcctggc tcaggacgaa cgctggcggc gtgcctaata catgcaagtc       60
gagcggacag aagggagctt gctcccggat gttagcggcg gacgggtgag taacacgtgg      120
gtaacctgcc tgtaagactg ggataactcc gggaaaccgg agctaatacc ggatagttcc      180
ttgaaccgca tggttcaagg atgaaagacg gtttcggctg tcacttacag atggacccgc      240
ggcgcattag ctagttggtg gggtaatggc tcaccaaggc gacgatgcgt agccgacctg      300
agagggtgat cggccacact gggactgaga cacggcccag actcctacgg gaggcagcag      360
tagggaatct tccgcaatgg acgaaagtct gacggagcaa cgccgcgtga gtgatgaagg      420
ttttcggatc gtaaagctct gttgttaggg aagaacaagt gcgagagtaa ctgctcgcac      480
cttgacggta cctaaccaga aagccacggc taactacgtg ccagcagccg cggtaatacg      540
taggtggcaa gcgttgtccg gaattattgg gcgtaaaggg ctcgcaggcg gtttcttaag      600
tctgatgtga aagcccccgg ctcaaccggg gagggtcatt ggaaactggg aaacttgagt      660
gcagaagagg agagtggaat tccacgtgta gcggtgaaat gcgtagagat gtggaggaac      720
accagtggcg aaggcgactc tctggtctgt aactgacgct gaggagcgaa agcgtgggga      780
gcgaacagga ttagataccc tggtagtcca cgccgtaaac gatgagtgct aagtgttagg      840
gggtttccgc cccttagtgc tgcagctaac gcattaagca ctccgcctgg ggagtacggt      900
```

```
cgcaagactg aaactcaaag gaattgacgg gggcccgcac aagcggtgga gcatgtggtt    960
taattcgaag caacgcgaag aaccttacca ggtcttgaca tcgtctgata accctagaga   1020
tagggctttc ccttcgggga cagagtgaca ggtggtgcat ggtcagtcgt cagctcgtgt   1080
cgtgagatgt tgggttaagt cccgcaacgg gcgcaaccct tgatcttagt tgccagcatt   1140
tagttgggca ctcttaaggt gactgccggt gacaaaccgg aggaaggtgg ggatgacgtc   1200
aaatcatcat gccccttatg acctgggcta cacacgtgct acaatggaca gaacaaaggg   1260
ctgcgagacc gcaaggttta gccaatccca taaatctgtt ctcagttcgg atcgcagtct   1320
gcaactcgac tgcgtgaagc tggaatcgct agtaatcgcg gatcagcatg ccgcggtgaa   1380
tacgttcccg ggccttgtac acaccgcccg tcacaccacg ggagtttgca cacccgaag   1440 tcggtgaggt aacctttatg gagccagccg ccgaaggtgg gcagatgat tggggtgaag   1500 tcgtaacaag gtaaccaatc actagt                                       1526

<210> SEQ ID NO 15
<211> LENGTH: 1526
<212> TYPE: DNA
<213> ORGANISM: Bacillus sp

<400> SEQUENCE: 15
gattagagtt tgatcatggc tcaggacgaa cgctggcggc gtgcctaata catgcaagtc     60
gagcggacag aagggagctt gctcccggat gttagcggcg gacgggtgag taacacgtgg    120
gtaacctgcc tgtgagactg ggataactcc gggaaaccgg agctaatacc ggatagttcc    180
ttgaaccgca tggttcaagg atgaaagacg gtttcggctg tcacttacag atggacccgc    240
ggcgcattag ctagttggtg gggtaatggc tcaccaaggc gacgatgcgt agccgacctg    300
agagggtgat cggccacact gggactgaga cacggcccag actcctacgg gaggcagcag    360
tagggaatct tccgcaatgg acgaaagtct gacggagcaa cgccgcgtga gtgatgaagg    420
ttttcggatc gtaaagctct gttgttgggg aagaacaagt gcgagagtaa ctgctcgcac    480
cttgacggta cctaaccaga aagccacggc taactacgtg ccagcagccg cggtaatacg    540
taggtggcaa gcgttgtccg gaattattgg gcgtaaaggg ctcgcaggcg gtttcttaag    600
tctgatgtga aagcccccgg ctcaaccggg gagggtcatt ggaaactggg aaacttgagt    660
gcagaagagg agagtggaat tccacgtgta gcggtgaaat gcgtagagat gtggaggaac    720
accagtggcg aaggcgactc tctggtctgt aactgacgct gaggagcgaa agcgtgggga    780
gcgaacagga ttagataccc tggtagtcca cgccgtaaac gatgagtgct aagtgttagg    840
gggtttccgc cccttagtgc tgcagctaac gcattaagca ctccgcctgg ggagtacggt    900
cgcaagactg aaactcaaag gaattgacgg gggcccgcac aagcggtgga gcatgtggtt    960
taattcgaag caacgcgaag aaccttacca ggtcttgaca tcctctgata accctagaga   1020
tagggctttc ccttcgggga cagagtgaca ggtggtgcat ggttgtcgtc agctcgtgtc   1080
gtgagatgtt gggttaagtc cgcaacgag cgcaggggg ggggcttag tagccagcat   1140 ttagttgggc actctaaggt gactgccggt gacaaaccgg aggaaggtgg ggatgacgtc   1200
aaatcatcat gccccttatg acctgggcca cacacgtgct acaatggaca gaacaaaggg   1260
ctgcgagacc gcaaggttta gccaatccca taaatctgtt ctcagttcgg atcgcagtct   1320
gcaactcgac tgcgtgaagc tggaatcgct agtaatcgcg gatcagcatg ccgcggtgaa   1380
tacgttcccg ggccttgtgc acaccgcccg tcacaccacg agagtttgca cacccgaag   1440
```

```
tcggtgaggt aaccattatg gagccagccg ccgaaggtgg ggcagatgat tggggtgaag    1500
tcgtaacaag gtaaccaatc actagt                                        1526

<210> SEQ ID NO 16
<211> LENGTH: 1524
<212> TYPE: DNA
<213> ORGANISM: Bacillus licheniformis

<400> SEQUENCE: 16
actagtgatt agagtttgat cctggctcag gacgaacgct ggcggcgtgc ctaatacatg     60
caagtcgagc ggacagatgg gagcttgctc cctgatgtta gcggcggacg ggtgagtaac    120
acgtgggtaa cctgcctgta agactgggat aactccggga aaccggggct aataccggat    180
gcttgattga accgcatggt tcaattataa aaggtggctt cggctaccac ttacagatgg    240
acccgcggcg cattagctag ttggtgaggt aacggctcac caaggcaacg atgcgtagcc    300
gacctgagag ggtgatcggc cacactggga ctgagacacg gcccagactc ctacgggagg    360
cagcagtagg gaatcttccg caatggacga aagtctgacg gagcaacgcc gcgtgagtga    420
tgaaggtttt cggatcgtaa aactctgttg ttagggaaga acaagtaccg ttcgaatagg    480
gcggtacctt gacggtacct aaccagaaag ccacggctaa ctacgtgcca gcagccgcgg    540
taatacgtag gtggcaagcg ttgtccggaa ttattgggcg taaagcgcgc gcaggcggtt    600
tcttaagtct gatgtgaaag ccccggctc aaccggggag ggtcattgga aactggggaa    660
cttgagtgca gaagaggaga gtggaattcc acgtgtagcg gtgaaatgcg tagagatgtg    720
gaggaacacc agtggcgaag gcgactctct ggtctgtaac tgacgctgag gcgcgaaggc    780
gtggggagcg aacaggatta gataccctgg tagtccacgc cgtaaacgat gagtgctaag    840
tgttagaggg tttccgccct ttagtgctgc agcaaacgca ttaagcactc cgcctgggga    900
gtacggtcgc aagactgaaa ctcaaaggaa ttgacggggg cccgcacaag cggtggagca    960
tgtggtttaa ttcgaagcaa cgcgaagaac cttaccaggt cttgacatcc tctgacaacc   1020
ctagagatag gcttcccct tcgggggcag agtgacaggt ggtgcatggt tgtcgtcagc   1080
tcgtgtcgtg agatgttggg ttaagtcccg caacgagcgc aacccttgat cttagttgcc   1140
agcattcagt tgggcactct aaggtgactg ccggtgacaa accggaggaa ggtggggatg   1200
acgtcaaatc atcatgcccc ttatgacctg ggctacacac gtgctacaat gggcagaaca   1260
aagggcagcg aagccgcgag gctaagccaa tcccacaaat ctgttctcag ttcggatcgc   1320
agtctgcaac tcgactgcgt gaagctggaa tcgctagtaa tcgcggatca gcatgccgcg   1380
gtgaatacgt tcccgggcct tgtacacacc gcccgtcaca ccacgagagt ttgtaacacc   1440
cgaagtcggt gaggtaacct tttggagcca gccgccgaag gtgggacaga tgattggggt   1500
gaagtcgtaa caaggtaacc aatc                                          1524
```

What is claimed is:

1. A consortium of microorganisms capable of hydrolyzing cellulose, characterized in that it comprises:
   - a mixture of *Bacillus* sp. KP7, KP20 and *Ochrobactrum* sp. KP8 deposited in PCM under the no. B/00064;
   - a mixture of *Providencia* sp. KP14; *Bacillus* sp. KP6 and KP16 deposited in PCM under the no. B/00065;
   - a mixture of *Bacillus* sp. KP4, KP5, KP17 and KP22 deposited in PCM under the no. B/00066;
   - a mixture of *Providencia* sp. KP10; *Bacillus* sp. KP1 and KP19 deposited in PCM under the no. B/00067; and
   - a mixture of *Ochrobactrum* sp. KP13; *Bacillus* sp. KP9 and KP12 deposited in PCM under the no. B/00068.

2. The consortium of microorganisms according to claim 1, characterized in that the individual strains in each mixture are mixed in equal proportions.

3. The consortium of microorganisms according to claim 2, characterized in that all the mixtures are mixed in an equal quantitative ratio.

4. A preparation for hydrolysis of cellulose, increasing the efficiency of biogas production in methane fermentation process, revival and/or propagation of methanogenic consortia and/or methanogenic microorganisms themselves, characterized in that it comprises the consortium of microorganisms according to claim 1.

5. The preparation of claim 4, wherein the cellulose is lignocellulosic biomass.

6. The preparation according to claim 4, wherein the preparation also comprises supplementary and/or auxiliary substances.

7. A combination preparation for catalyzing hydrolysis of cellulose, increasing the efficiency of biogas production in methane fermentation process and/or for revival and/or propagation of methanogenic consortia and/or methanogenic microorganisms themselves, comprising a combination of: a) the consortium of microorganisms capable of hydrolyzing cellulose according to claim 1 and b) a supplement preparation for supplementing methane fermentation comprising organic and inorganic substances from the degradation of biomass, produced with the consortium of microorganisms according to claim 1.

8. The combination preparation of claim 7, wherein the cellulose is lignocellulosic biomass.

9. A method of catalyzing hydrolysis of cellulose comprising adding the consortium of microorganisms according to claim 1 to cellulose.

10. The method of claim 9, wherein the cellulose is lignocellulosic biomass.

11. The method according to claim 9, wherein the method leads to an increased efficiency of biogas production in methane fermentation process.

12. The method according to claim 9, further comprising dispensing the consortium of microorganisms directly in digesters.

13. The method according to claim 9, wherein the hydrolysis is carried out under anaerobic conditions at 30° C.

14. The method according to claim 9 wherein the hydrolysis is carried out at pH 7.

15. The method according to claim 9, wherein the consortium of microorganisms further comprises a methanogenic consortium.

16. A method of reviving or propagating methanogenic consortia, and/or methanogenic microorganisms, comprising adding the consortium of microorganisms according to claim 1 to methanogenic consortia, and/or methanogenic microorganisms.

* * * * *